United States Patent [19]

Tseng

[11] Patent Number: 4,604,133
[45] Date of Patent: Aug. 5, 1986

[54] HERBICIDAL SULFONAMIDE INNER SALTS

[75] Inventor: Chi-Ping Tseng, Wilmington, Del.

[73] Assignee: E. I. Du Pont de Nemours and Company, Wilmington, Del.

[21] Appl. No.: 670,967

[22] Filed: Nov. 13, 1984

Related U.S. Application Data

[60] Division of Ser. No. 551,004, Nov. 16, 1983, Pat. No. 4,484,939, which is a continuation-in-part of Ser. No. 467,650, Feb. 18, 1983, abandoned.

[51] Int. Cl.[4] ............... C07D 251/18; C07D 251/52; C07D 251/46; A01N 43/70
[52] U.S. Cl. ............ 71/90; 71/93; 260/96.5 R; 544/211; 544/212; 544/206; 544/207; 544/208; 544/209; 544/219
[58] Field of Search ......... 71/93, 90; 260/96.5 R; 544/211, 212, 206, 207, 208, 209, 219

[56] References Cited

U.S. PATENT DOCUMENTS 4,484,939  11/1984  Tseng ..................... 71/92

Primary Examiner—John M. Ford

[57] ABSTRACT

Certain sulfonamide inner salts, such as 2-[N-[(4,6-dimethylpyrimidin-2-yl)aminocarbonyl]aminosulfonyl]benzoic acid methyl ester, dimethylsulfonium inner salt, possess utility as herbicides.

14 Claims, No Drawings

HERBICIDAL SULFONAMIDE INNER SALTS

CROSS REFERENCE TO RELATED APPLICATION

This application is a division of application U.S. Ser. No. 551,004, filed Nov. 16, 1983, now U.S. Pat. No. 4484939, which is a continuation-in-part of my application U.S. Ser. No. 467,650, filed Feb. 18, 1983, now abandoned.

BACKGROUND OF THE INVENTION

This invention relates to novel sulfonamide inner salts, to herbicidal compositions containing them and to methods using them to control the growth of undesired vegetation.

U.S. Pat. No. 4,169,719 discloses herbicidal sulfonamides of the general formula

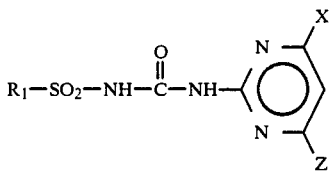

where $R_1$ can be substituted phenyl, optionally substituted thiophene or naphthalene. U.S. Pat. No. 4,127,405 discloses the corresponding triazine compounds. A number of additional patents or patent applications have issued or been published which disclose herbicidal sulfonamide derivatives, but no references are known which disclose the dialkylsulfonium inner salts of this invention.

SUMMARY OF THE INVENTION

Test results now indicate that the novel compounds of Formula I possess herbicidal activity.

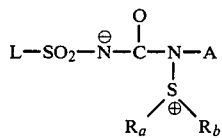

wherein
  $R_a$ is $CH_3$ or $CH_2CH_3$;
  $R_b$ is $CH_3$ or $CH_2CH_3$;
  L is

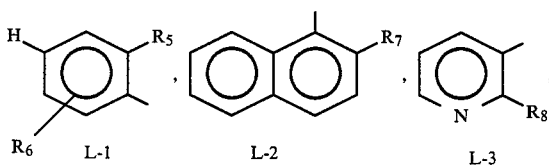

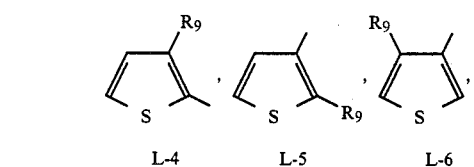

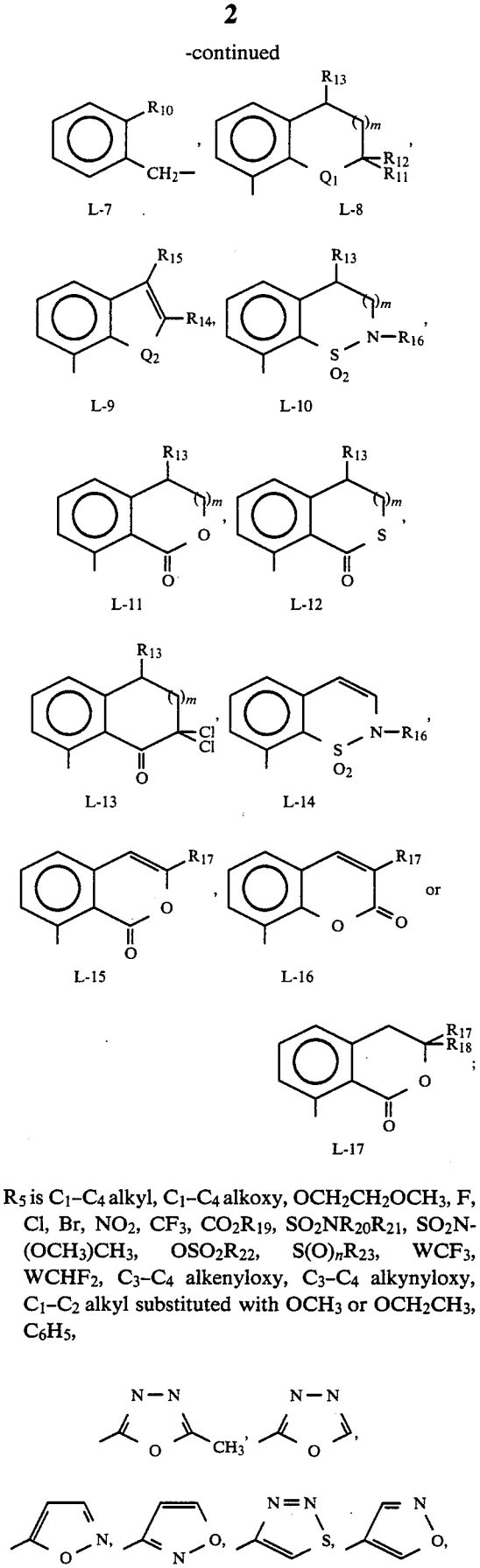

$R_5$ is $C_1$–$C_4$ alkyl, $C_1$–$C_4$ alkoxy, $OCH_2CH_2OCH_3$, F, Cl, Br, $NO_2$, $CF_3$, $CO_2R_{19}$, $SO_2NR_{20}R_{21}$, $SO_2N(OCH_3)CH_3$, $OSO_2R_{22}$, $S(O)_nR_{23}$, $WCF_3$, $WCHF_2$, $C_3$–$C_4$ alkenyloxy, $C_3$–$C_4$ alkynyloxy, $C_1$–$C_2$ alkyl substituted with $OCH_3$ or $OCH_2CH_3$, $C_6H_5$, -continued

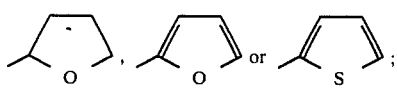

$R_6$ is H, F, Cl, Br, $CF_3$, $CH_3$, $OCH_3$, $SCH_3$ or $OCF_2H$;

$R_7$ is H, $CH_3$, $OCH_3$, F, Cl, Br, $OSO_2CH_3$ or $S(O)_nCH_3$;

$R_8$ is $CH_3$, $CH_2CH_3$, $OCH_3$, $OCH_2CH_3$, F, Cl, Br, $SO_2NR_{20}R_{21}$, $SO_2N(OCH_3)CH_3$ or $S(O)_nR_{23}$;

$R_9$ is $C_1$-$C_3$ alkyl, F, Cl, Br, $NO_2$, $CO_2R_{19}$, $SO_2NR_{20}R_{21}$, $SO_2N(OCH_3)CH_3$ or $S(O)_nR_{23}$;

$R_{10}$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_{11}$ is H, $CH_3$ or $CH_2CH_3$;
$R_{12}$ is H, $CH_3$ or $CH_2CH_3$;
$R_{13}$ is H or $CH_3$;
$R_{14}$ is H or $CH_3$;
$R_{15}$ is H or $CH_3$;
$R_{16}$ is $CH_3$ or $CH_2CH_3$;
$R_{17}$ is H or $CH_3$;
$R_{18}$ is H or $CH_3$;
$R_{19}$ is $C_1$-$C_4$ alkyl, $CH_2CH_2OCH_3$, $CH_2CH_2Cl$ or $CH_2CH=CH_2$;
$R_{20}$ is $C_1$-$C_3$ alkyl;
$R_{21}$ is $C_1$-$C_3$ alkyl;
$R_{22}$ is $C_1$-$C_3$ alkyl or $N(CH_3)_2$;
$R_{23}$ is $C_1$-$C_3$ alkyl or $CH_2CH=CH_2$;
m is 0 or 1;
n is 0 or 2;
$Q_1$ is O, S, $SO_2$ or $NR_{17}$;
$Q_2$ is O, S or $NR_{17}$; and
W is O, S or $SO_2$;

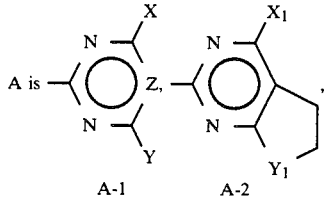

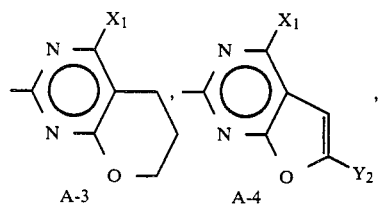

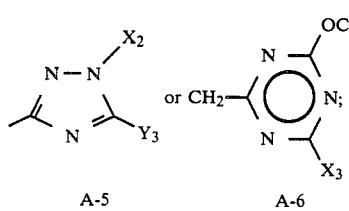

X is $CH_3$, $OCH_3$, $OCH_2CH_3$, Cl, F, Br, $OCF_2H$, $CH_2F$ or $CF_3$;

Y is H, $CH_3$, $OCH_3$, $OCH_2CH_3$, $CH_2OCH_3$, $CH_2OCH_2CH_3$, $N(CH_3)_2$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$, $CR_{24}(QCH_3)_2$,

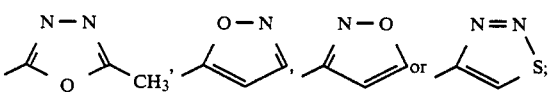

or $CR_{24}(QCH_2CH_3)_2$;

Q is O or S;
$R_{24}$ is H or $CH_3$;
Z is CH or N;
$Y_1$ is $CH_2$ or O;
$X_1$ is $CH_3$, $OCH_3$, $OCH_2CH_3$ or $OCF_2H$;
$Y_2$ is H or $CH_3$;
$X_2$ is $CH_3$, $CH_2CH_3$ or $CH_2CF_3$;
$Y_3$ is $OCH_3$, $OCH_2CH_3$, $SCH_3$, $CH_3$ or $CH_2CH_3$;
$X_3$ is $CH_3$ or $OCH_3$; provided that (1) the total number of carbon atoms of $R_{20}$ and $R_{21}$ is less than or equal to four;
(2) when m is 1, then $R_{13}$ is H; and
(3) when L is L-17, then $R_{17}$ and $R_{18}$ are not simultaneously H;
(4) when X is Cl, F or Br, then Z is CH and Y is $OCH_3$, $OCH_2CH_3$, $N(CH_3)_2$ or $OCF_2H$;

This invention therefore relates to the novel compounds of Formula I, to herbicidal compositions containing them and to methods of using them to control the growth of undesired vegetation.

Certain groups of compounds within the scope of this invention are preferred for reasons of their high herbicidal activity and/or ease of synthesis. These preferred groups are:

(1) Compounds of Formula I where A is A-1.
(2) Compounds of Preferred 1 where Y is $CH_3$, $OCH_3$, $OCH_2CH_3$, $CH_2OCH_3$, $OCH_2CF_3$ or $CH(OCH_3)_2$ and X is $CH_3$, $OCH_3$, Cl or $CF_3$.
(3) Compounds of Preferred 2 where L is L-1, L-2, L-3, L-5, L-8, L-10, L-11, L-16 or L-17.
(4) Compounds of Preferred 3 where L is L-1, $R_5$ is $OCH_3$, $OCH_2CH_3$, Cl, $NO_2$, $CF_3$, $CO_2CH_3$, $CO_2CH_2CH_3$, $SO_2N(CH_3)_2$, $SO_2N(OCH_3)CH_3$, $OSO_2R_{22}$, $S(O)_nR_{23}$, $OCF_2H$, $SCF_2H$, $OCH_2CH=CH_2$, $OCH_2C\equiv CH$, $$\underset{O}{\overset{N-N}{\diagdown}}, \underset{CH_3}{\overset{O-N}{\diagdown}}, \underset{}{\overset{N-O}{\diagdown}} \text{or} \underset{S}{\overset{N=N}{\diagdown}};$$

$R_{22}$ is $C_1$-$C_3$ alkyl; $R_{23}$ is $CH_3$ and n is 2.
(5) Compounds of Preferred 3 where L is L-2 and $R_7$ is Cl, $CH_3$, $OCH_3$, $SCH_3$ or Br.
(6) Compounds of Preferred 3 where L is L-3 and $R_8$ is Cl, $SO_2CH_3$ or $SO_2N(CH_3)_2$.
(7) Compounds of Preferred 3 where L is L-5 and $R_9$ is $CO_2CH_3$ or $CO_2CH_2CH_3$.
(8) Compounds of Preferred 3 where L is L-8.
(9) Compounds of Preferred 3 where L is L-10.
(10) Compounds of Preferred 3 where L is L-11.
(11) Compounds of Preferred 3 where L is L-16.
(12) Compounds of Preferred 3 where L is L-17.

Specifically preferred for reasons of their highest herbicidal activity and/or most favorable ease of synthesis are:

2-[[(4-methoxy-6-methylpyrimidin-2-yl)aminocarbonyl]aminosulfonyl]benzoic acid methyl ester, dimethylsulfonium inner salt, m.p. 90°–91° (d);

2-[[(4,6-dimethoxypyrimidin-2-yl)aminocarbonyl]aminosulfonyl]benzoic acid methyl ester, dimethylsulfonium inner salt, m.p. 88°–90° (d);

N-[(4,6-dimethylpyrimidin-2-yl)aminocarbonyl]-2-methylsulfonylbenzenesulfonamide, dimethylsulfonium inner salt, m.p. 90°–91° (d);

2-[[(4,6-dimethylpyrimidin-2-yl)aminocarbonyl]aminosulfonyl]benzoic acid methyl ester, dimethylsulfonium inner salt, m.p. 88°–90° (d); and N-[(4,6-dimethoxypyrimidin-2-yl)aminocarbonyl]-2-dimethylaminosulfonylbenzenesulfonamide, dimethylsulfonium inner salt, m.p. 173°–175° (d).

DETAILED DESCRIPTION OF THE INVENTION

Synthesis

The compounds of Formula I can be prepared by contacting an appropriate sulfonyl isocyanate III with an S,S-dialkyl-N-(heterocyclic)sulfilimine II as illustrated in Equation 1. (L, $R_a$, $R_b$ and A are as previously defined.)

Equation 1

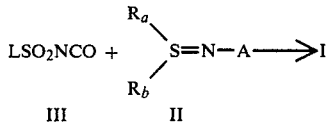

III  II

The reaction of Equation 1 is best carried out in an inert aprotic solvent, such as methylene chloride, tetrahydrofuran, acetonitrile, ether or chloroform, at temperatures ranging from about −20° to 50° C. In some cases, the desired product may crystallize from the reaction medium and may be filtered. Reaction products which are soluble in the reaction medium may be isolated by evaporation of the solvent, trituration of the residue with solvents such as diethyl ether, ethyl acetate, 1-chlorobutane or hexane. Chromatography (e.g., silica gel) may also be necessary for purification.

The sulfonyl isocyanates III used as starting materials are generally known in the art and can be prepared by known methods. One method involves reacting an appropriate benzene or heterocyclic sulfonamide with phosgene in the presence of an alkyl isocyanate, such as n-butyl isocyanate, and a tertiary amine catalyst, such as 1,4-diazabicyclo[2.2.2]octane, at reflux in a solvent such as xylene or chlorobenzene. See H. Ulrich and A. A. Y. Sayigh, *Newer Methods of Preparative Organic Chemistry*, Vol. VI, p. 223–241, Academic Press, New York and London, W. Foerst Ed.

The sulfonyl isocyanates III can also be prepared from sulfonamides by a two step procedure involving (a) reacting the sulfonamides with an alkyl isocyanate in the presence of a base such as $K_2CO_3$ at reflux in an inert solvent such as 2-butanone, forming an alkylsulfonylurea, and (b) reacting this compound with phosgene and tertiary amine catalyst at reflux in xylene solvent.

The preparation of sulfonamides from ammonium hydroxide and sulfonyl chlorides is widely reported in the literature, e.g. Crossley et al., *J. Am. Chem. Soc.*, 60, 2223 (1938). Certain sulfonyl chlorides are best prepared by chlorosulfonation of a substituted benzene, naphthalene, or thiophene in carbon tetrachloride according to the teaching of H. T. Clarke et al., *Org. Synth. Coll.*, Vol. 1, 2nd Ed. 1941, p. 85. Other sulfonyl chlorides can be made by diazotization of the appropriate amine with sodium nitrite in HCl, followed by reaction of the diazonium salt with sulfur dioxide and cuprous chloride in acetic acid according to the teachings of H. L. Yale and F. Sowinski, *J. Org. Chem.* 25, 1824 (1960).

Reference to the following patents and patent applications, the disclosures of which are hereby incorporated by reference, is suggested for further details regarding the preparation of the sulfonyl isocyanates III: U.S. Pat. No. 4,169,719, U.S. Pat. No. 4,127,405; U.S. Pat. No. 4,383,113; U.S. Pat. No. 4,394,506; U.S. Pat. No. 4,120,691; U.S. Pat. No. 4,238,621; European Patent Application No. 80304286.0, published June 10, 1981; European Patent Application No. 79302769.9, published July 23, 1980; Canadian Pat. No. 1128042; European Patent Application 82301500.3, published Nov. 17, 1982; European Patent Application 81305160.4, published May 12, 1982; and copending U.S. patent applications Ser. No. 410,993, filed Aug. 27, 1982; U.S. Ser. No. 406,191, filed Aug. 11, 1982, U.S. Ser. No. 499,443, filed May 31, 1983, and U.S. Ser. No. 436,631, filed Oct. 10, 1982.

The sulfilimine (II) starting materials may be made in a number of ways. S,S-Dimethyl-N-(4,6-dimethylpyrimidin-2-yl)sulfilimine and S,S-dimethyl-N-(4-methylpyrimidin-2-yl)sulfilimine are taught by T. L. Gilchrist, C. J. Harris and C. W. Rees in *J.C.S. Chem. Comm.*, 486 (1974). The procedure taught in this article can be adapted to prepare other sulfilimines of Formula II as shown in Equation 2.

Equation 2

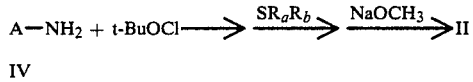

IV

A heterocyclic amine IV is contacted successively with tert-butyloxy chloride, a dialkylmercaptide and sodium methoxide.

The reaction may be best carried out in an inert aprotic solvent, such as methylene chloride, chloroform or ethyl acetate at temperatures between −60° to 60° C. for 1–48 hours with ambient pressure. The resulting solution may be washed with water. In some cases, the desired product may crystallize from the organic solvent and may be filtered. Reaction products which are soluble in the organic solvent may be isolated by evaporation of the solvent after the organic solution is dried over a drying agent such as sodium sulfate or magnesium sulfate and trituration of the residue with solvents such as diethyl ether, 1-chlorobutane or hexane. Chromatography (e.g., silica gel) may also be necessary for purification.

Sulfilimines of Formula II can also be prepared by the general procedure illustrated in Equation 3.

Equation 3

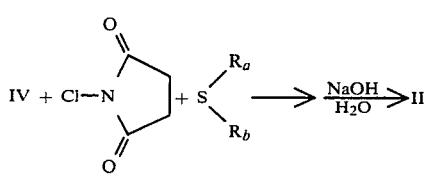

The appropriate amine IV is contacted with the appropriate dialkylmercaptide in the presence of N-chlorosuccinimide.

The reaction is best carried out in an inert aprotic solvent, such as methylene chloride, chloroform or ethyl acetate at temperatures between −30° to 60° C. for 1–48 hours with ambient pressure. The resulting solution is then washed with aqueous sodium hydroxide solution and then water. The desired product can be isolated as described in the previous paragraph.

Yet another method for preparing the sulfilimines II is shown in Equation 4.

Equation 4

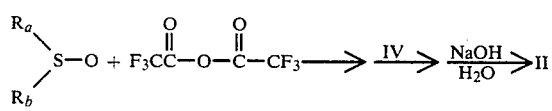

The reaction of Equation 4 may be best carried out in an inert aprotic solvent, such as methylene chloride or chloroform at temperatures between −70° to 70° C. for 1–48 hours with ambient pressure. The resulting solution may be washed with sodium hydroxide aqueous solution and then water. The desired product can be isolated as described in the previous paragraph.

Heterocyclic amines of Formula IV and methods for preparing them are known in the art. The synthesis of heterocyclic amines such as those of Formula IV has been reviewed in "The Chemistry of Heterocyclic Compounds", a series published by Interscience Publ., New York and London. 2-Aminopyrimidines are described by D. J. Brown in "The Pyrimidines", Vol. XVI of this series. 2-Amino-1,3,5-triazines can be prepared according to methods described by E. M. Smolin and L. Rapaport in "s-Triazines and Derivatives", Vol. XIII of the same series. The synthesis of triazines is also described by F. C. Schaefer, U.S. Pat. No. 3,154,547 and by K. R. Huffman and F. C. Schaefer; *J. Org. Chem.*, 28, 1816 (1963). See also U.S. Ser. No. 434,038, filed Oct. 20, 1982, European Patent Application No. 80300505.7, published Sept. 17, 1980 (Pub. No. 15,683), European Patent Application No. 81303837.9, published Mar. 3, 1982 (Pub. No. 46,677), European Patent Application No. 82306492.8, published July 27, 1983 (Pub. No. 84,224), and European Patent Application No. 82303611.6, published Mar. 9, 1983 (Pub. No. 73,562), for description of methods for preparing heterocyclic amine derivatives.

EXAMPLE 1

Preparation of S,S-dimethyl-N-(4,6-dimethylpyrimidin-2-yl)sulfilimine

To a solution of 12.3 g (0.10 mole) of 2-amino-4,6-dimethylpyrimidine and 8 ml (0.109 mole) of methylsulfide in 100 ml of methylene chloride at −20° C. was added dropwise a solution of 13.3 g (0.10 mole) of N-chlorosuccinimide in 300 ml of methylene chloride. After addition, the resulting solution was warmed to room temperature and was kept at room temperature for one hour with stirring. The solution was then washed with 400 ml of 2.5% sodium hydroxide aqueous solution and then 400 ml of water. This solution was dried over sodium sulfate and filtered. The filtrate was washed with ethyl ether, and dried under vacuum at ambient temperature to afford 4 g of the title compound as a white solid, m.p. 117°–120° C.

NMR: $\delta 2.23$ (s, $CH_3$); $\delta 2.7$ (s, $SCH_3$); and $\delta 6.23$ (s, ArH).

EXAMPLE 2

Preparation of S,S-dimethyl-N-(4,6-dimethoxypyrimidin-2-yl)sulfilimine

To a solution of 15.5 g (0.10 mole) of 2-amino-4,6-dimethoxypyrimidine and 8 ml (0.109 mole) of methylsulfide in 100 ml of methylene chloride at −20° C. was added dropwise a solution of 13.3 g (0.10 mole) of N-chlorosuccinimide in 300 ml of methylene chloride. After addition, the resulting solution stirred at −20° C. for 2 hours and then warmed up to room temperature. The solution was stirred at room temperature for another hour. The solution was washed with 400 ml of 2.5% sodium hydroxide aqueous solution and then 400 ml of water. The organic layer was separated, dried over sodium sulfate and concentrated under reduced pressure. The residue was washed with ethyl ether, and dried under vacuum at ambient temperature to afford 6 g of the title compound as a solid, m.p. 102°–103° C. (dec.).

NMR: $\delta 2.73$ (s, $SCH_3$); $\delta 3.9$ (s, $OCH_3$); and $\delta 5.37$ (s, ArH).

EXAMPLE 3

[[N-(2-Chlorophenylsulfonylaminocarbonyl)-N-(4,6-dimethylpyrimidin-2-yl)]amino]dimethylsulfonium inner salt To a solution of 0.6 g (0.0033 mole) of S,S-dimethyl-N-(4,6-dimethylpyrimidin-2-yl)sulfilimine in 15 ml of methylene chloride was added 1.5 g (0.0069 mole) of 2-chlorophenylsulfonyl isocyanate.

The resulting solution was stirred at ambient temperature for 12 hours. The solution was then concentrated under reduced pressure. The residue was washed with 1-chlorobutane, ethyl ether and ethyl acetate. The solid was collected by filtration and dried under vacuum to afford 1.1 g of the title compound, m.p. 104°–105° C. (dec.).

NMR: $\delta 2.43$ (s, $CH_3$); $\delta 2.87$ (s, $SCH_3$); and $\delta 6.5$–$8.5$ (m, ArH).

Using procedures analogous to that described in Example 3, the following compounds can be prepared.

TABLE I

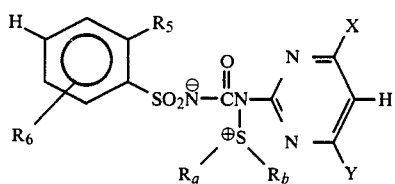

| $R_5$ | $R_a$ | $R_b$ | $R_6$ | X | Y | m.p. (°C.) |
|---|---|---|---|---|---|---|
| $CO_2CH_3$ | $CH_3$ | $CH_3$ | H | $CH_3$ | $CH_3$ | 88–90° (d) |
| $CO_2CH_2CH_3$ | $CH_3$ | $CH_3$ | H | $CH_3$ | $CH_3$ | |
| $CO_2CH_3$ | $C_2H_5$ | $C_2H_5$ | H | $CH_3$ | $CH_3$ | |
| $CO_2CH_3$ | $C_2H_5$ | $CH_3$ | H | $CH_3$ | $CH_3$ | |
| $CO_2CH_2CH_2CH_2CH_3$ | $CH_3$ | $CH_3$ | H | $CH_3$ | $CH_3$ | |
| $CO_2CH_2CH=CH_2$ | $CH_3$ | $CH_3$ | H | $CH_3$ | $CH_3$ | |
| $CO_2CH_2CH_2OCH_3$ | $CH_3$ | $CH_3$ | H | $CH_3$ | $CH_3$ | |
| $CO_2CH_2CH_2Cl$ | $CH_3$ | $CH_3$ | H | $CH_3$ | $CH_3$ | |
| $SCH_3$ | $CH_3$ | $CH_3$ | H | $CH_3$ | $CH_3$ | |
| $SCH_2CH_3$ | $CH_3$ | $CH_3$ | H | $CH_3$ | $CH_3$ | |
| $SCH(CH_3)_2$ | $CH_3$ | $CH_3$ | H | $CH_3$ | $CH_3$ | |
| $SCH_2CH=CH_2$ | $CH_3$ | $CH_3$ | H | $CH_3$ | $CH_3$ | |
| $SCF_3$ | $CH_3$ | $CH_3$ | H | $CH_3$ | $CH_3$ | |
| $SCF_2H$ | $CH_3$ | $CH_3$ | H | $CH_3$ | $CH_3$ | |
| $SO_2CH_3$ | $CH_3$ | $CH_3$ | H | $CH_3$ | $CH_3$ | 90–91° (d) |
| $SO_2CH_2CH_3$ | $CH_3$ | $CH_3$ | H | $CH_3$ | $CH_3$ | |
| $SO_2CH_3$ | $C_2H_5$ | $C_2H_5$ | H | $CH_3$ | $CH_3$ | |
| $SO_2CH_3$ | $C_2H_5$ | $CH_3$ | H | $CH_3$ | $CH_3$ | |
| $SO_2CF_3$ | $CH_3$ | $CH_3$ | H | $CH_3$ | $CH_3$ | |
| $SO_2CF_2H$ | $CH_3$ | $CH_3$ | H | $CH_3$ | $CH_3$ | |
| $OSO_2CH_3$ | $CH_3$ | $CH_3$ | H | $CH_3$ | $CH_3$ | |
| $OSO_2CH_2CH_3$ | $CH_3$ | $CH_3$ | H | $CH_3$ | $CH_3$ | |
| $OSO_2CH(CH_3)_2$ | $CH_3$ | $CH_3$ | H | $CH_3$ | $CH_3$ | |
| $OCH_3$ | $CH_3$ | $CH_3$ | H | $CH_3$ | $CH_3$ | |
| $OCH_2CH_3$ | $CH_3$ | $CH_3$ | H | $CH_3$ | $CH_3$ | |
| $OCH_2CH_2CH_3$ | $CH_3$ | $CH_3$ | H | $CH_3$ | $CH_3$ | |
| $OCH(CH_3)CH_2CH_3$ | $CH_3$ | $CH_3$ | H | $CH_3$ | $CH_3$ | |
| $OCH_2CH=CH_2$ | $CH_3$ | $CH_3$ | H | $CH_3$ | $CH_3$ | |
| $OCH_2CH_2CH=CH_2$ | $CH_3$ | $CH_3$ | H | $CH_3$ | $CH_3$ | |
| $OCH(CH_3)CH=CH_2$ | $CH_3$ | $CH_3$ | H | $CH_3$ | $CH_3$ | |
| $SO_2N(CH_3)_2$ | $CH_3$ | $CH_3$ | H | $CH_3$ | $CH_3$ | |
| $SO_2N(CH_3)CH(CH_3)_2$ | $CH_3$ | $CH_3$ | H | $CH_3$ | $CH_3$ | |
| $SO_2N(OCH_3)CH_3$ | $CH_3$ | $CH_3$ | H | $CH_3$ | $CH_3$ | |
| $CH_2OCH_3$ | $CH_3$ | $CH_3$ | H | $CH_3$ | $CH_3$ | |
| $CH_2CH_2OCH_3$ | $CH_3$ | $CH_3$ | H | $CH_3$ | $CH_3$ | |
| F | $CH_3$ | $CH_3$ | H | $CH_3$ | $CH_3$ | |
| Cl | $CH_3$ | $CH_3$ | H | $CH_3$ | $CH_3$ | 104–105° (d) |
| Br | $CH_3$ | $CH_3$ | H | $CH_3$ | $CH_3$ | |
| $NO_2$ | $CH_3$ | $CH_3$ | H | $CH_3$ | $CH_3$ | 118–120° (d) |
| $CF_3$ | $CH_3$ | $CH_3$ | H | $CH_3$ | $CH_3$ | |
| $CH_3$ | $CH_3$ | $CH_3$ | H | $CH_3$ | $CH_3$ | |
| $CH_2CH_3$ | $CH_3$ | $CH_3$ | H | $CH_3$ | $CH_3$ | |
| $CH(CH_3)_2$ | $CH_3$ | $CH_3$ | H | $CH_3$ | $CH_3$ | |
| $CH_2CH_2CH_2CH_3$ | $CH_3$ | $CH_3$ | H | $CH_3$ | $CH_3$ | |
| $CO_2CH_2CH_2CH_3$ | $CH_3$ | $CH_3$ | H | $CH_3$ | $CH_3$ | |
| $SCH_3$ | $C_2H_5$ | $C_2H_5$ | H | $CH_3$ | $CH_3$ | |
| $SCF_3$ | $C_2H_5$ | $CH_3$ | H | $CH_3$ | $CH_3$ | |
| $SO_2CH_2CH_3$ | $C_2H_5$ | $C_2H_5$ | H | $CH_3$ | $CH_3$ | |
| $NO_2$ | $CH_3$ | $CH_3$ | H | $CH_3$ | $CH_3$ | |
| $CF_3$ | $CH_3$ | $CH_3$ | H | $CH_3$ | $CH_3$ | |
| $CH_3$ | $CH_3$ | $CH_3$ | H | $CH_3$ | $CH_3$ | |
| $NO_2$ | $CH_3$ | $CH_3$ | 5-$CF_3$ | $CH_3$ | $CH_3$ | |
| $NO_2$ | $CH_3$ | $CH_3$ | 3-Cl | $CH_3$ | $CH_3$ | |
| Cl | $CH_3$ | $CH_3$ | 6-$SCH_3$ | $CH_3$ | $CH_3$ | |
| $CF_3$ | $CH_3$ | $CH_3$ | 5-$SCH_3$ | $CH_3$ | $CH_3$ | |
| Cl | $CH_3$ | $CH_3$ | 5-Cl | $CH_3$ | $CH_3$ | |
| $NO_2$ | $CH_3$ | $CH_3$ | 5-Cl | $CH_3$ | $CH_3$ | |
| $SO_2N(CH_3)_2$ | $C_2H_5$ | $C_2H_5$ | 3-Cl | $CH_3$ | $CH_3$ | |
| $CO_2CH_3$ | $CH_3$ | $CH_3$ | 5-$CH_3$ | $CH_3$ | $CH_3$ | |
| Cl | $CH_3$ | $CH_3$ | 3-Br | $CH_3$ | $CH_3$ | |
| Cl | $CH_3$ | $CH_3$ | 5-Br | $CH_3$ | $CH_3$ | |
| $NO_2$ | $CH_3$ | $CH_3$ | 6-F | $CH_3$ | $CH_3$ | |
| Cl | $CH_3$ | $CH_3$ | 6-F | $CH_3$ | $CH_3$ | |
| Br | $CH_3$ | $CH_3$ | 3-F | $CH_3$ | $CH_3$ | |
| $NO_2$ | $C_2H_5$ | $C_2H_5$ | 5-$OCF_2H$ | $CH_3$ | $CH_3$ | |
| $CO_2CH_3$ | $CH_3$ | $CH_3$ | 3-$OCH_3$ | $CH_3$ | $CH_3$ | |
| $CH_3$ | $CH_3$ | $CH_3$ | 3-$OCH_3$ | $CH_3$ | $CH_3$ | |
| $CO_2CH_3$ | $CH_3$ | $CH_3$ | H | Cl | $OCH_3$ | |
| $NO_2$ | $CH_3$ | $CH_3$ | H | Cl | $OCH_3$ | |
| Cl | $CH_3$ | $CH_3$ | H | Cl | $OCH_3$ | |
| $CO_2CH_3$ | $C_2H_5$ | $CH_3$ | H | $CH_3$ | $OCH_3$ | |

TABLE I-continued

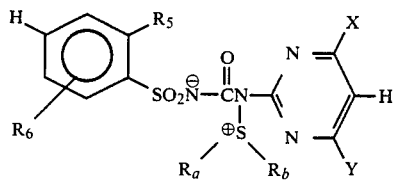

| $R_5$ | $R_a$ | $R_b$ | $R_6$ | X | Y | m.p. (°C.) |
|---|---|---|---|---|---|---|
| $CO_2CH_3$ | $C_2H_5$ | $C_2H_5$ | H | $CH_3$ | $OCH_3$ | |
| $NO_2$ | $C_2H_5$ | $CH_3$ | H | $CH_3$ | $OCH_3$ | |
| $SO_2N(CH_3)_2$ | $C_2H_5$ | $CH_3$ | H | $CH_3$ | $OCH_3$ | |
| $CO_2CH_3$ | $CH_3$ | $CH_3$ | H | $CH_3$ | $CH_2OCH_3$ | |
| $CO_2CH_3$ | $CH_3$ | $CH_3$ | H | $CH_3$ | $CH(OCH_3)_2$ | |
| $CO_2CH_3$ | $CH_3$ | $CH_3$ | H | $CH_3$ | $CH(OCH_2CH_2O)$ | |
| $NO_2$ | $C_2H_5$ | $C_2H_5$ | H | $CH_3$ | $OCH_3$ | |
| $SO_2N(CH_3)_2$ | $C_2H_5$ | $C_2H_5$ | H | $CH_3$ | $OCH_3$ | |
| $CO_2CH_3$ | $CH_3$ | $CH_3$ | H | $CH_3$ | $OCH_3$ | 90–91° (d) |
| $CO_2CH_2CH_3$ | $CH_3$ | $CH_3$ | H | $CH_3$ | $OCH_3$ | |
| $CO_2CH_2CH_2CH_3$ | $CH_3$ | $CH_3$ | H | $CH_3$ | $OCH_3$ | |
| $CO_2CH(CH_3)_2$ | $CH_3$ | $CH_3$ | H | $CH_3$ | $OCH_3$ | |
| $CO_2CH_2CH_2CH_2CH_3$ | $CH_3$ | $CH_3$ | H | $CH_3$ | $OCH_3$ | |
| $CO_2CH_2CH=CH_2$ | $CH_3$ | $CH_3$ | H | $CH_3$ | $OCH_3$ | |
| $CO_2CH_2CH_2OCH_3$ | $CH_3$ | $CH_3$ | H | $CH_3$ | $OCH_3$ | |
| $CO_2CH_2CH_2Cl$ | $CH_3$ | $CH_3$ | H | $CH_3$ | $OCH_3$ | |
| $SCH_3$ | $CH_3$ | $CH_3$ | H | $CH_3$ | $OCH_3$ | |
| $SCH_2CH_3$ | $CH_3$ | $CH_3$ | H | $CH_3$ | $OCH_3$ | |
| $SCH(CH_3)_2$ | $CH_3$ | $CH_3$ | H | $CH_3$ | $OCH_3$ | |
| $SCH_2CH=CH_2$ | $CH_3$ | $CH_3$ | H | $CH_3$ | $OCH_3$ | |
| $SCF_3$ | $CH_3$ | $CH_3$ | H | $CH_3$ | $OCH_3$ | |
| $SCF_2H$ | $CH_3$ | $CH_3$ | H | $CH_3$ | $OCH_3$ | |
| $SO_2CH_3$ | $CH_3$ | $CH_3$ | H | $CH_3$ | $OCH_3$ | |
| $SO_2CH_2CH_3$ | $CH_3$ | $CH_3$ | H | $CH_3$ | $OCH_3$ | |
| $SO_2CH(CH_3)_2$ | $CH_3$ | $CH_3$ | H | $CH_3$ | $OCH_3$ | |
| $SO_2CH_2CH=CH_2$ | $CH_3$ | $CH_3$ | H | $CH_3$ | $OCH_3$ | |
| $SO_2CF_3$ | $CH_3$ | $CH_3$ | H | $CH_3$ | $OCH_3$ | |
| $SO_2CF_2H$ | $CH_3$ | $CH_3$ | H | $CH_3$ | $OCH_3$ | |
| $OSO_2CH_3$ | $CH_3$ | $CH_3$ | H | $CH_3$ | $OCH_3$ | |
| $OSO_2CH_2CH_3$ | $CH_3$ | $CH_3$ | H | $CH_3$ | $OCH_3$ | |
| $OSO_2CH(CH_3)_2$ | $CH_3$ | $CH_3$ | H | $CH_3$ | $OCH_3$ | |
| $OCH_3$ | $CH_3$ | $CH_3$ | H | $CH_3$ | $OCH_3$ | |
| $OCH_2CH_3$ | $CH_3$ | $CH_3$ | H | $CH_3$ | $OCH_3$ | |
| $OCH(CH_3)_2$ | $CH_3$ | $CH_3$ | H | $CH_3$ | $OCH_3$ | |
| $OCH_2CH_2CH_2CH_3$ | $CH_3$ | $CH_3$ | H | $CH_3$ | $OCH_3$ | |
| $OCH_2CH=CH_2$ | $CH_3$ | $CH_3$ | H | $CH_3$ | $OCH_3$ | |
| $OCH_2CH_2CH=CH_2$ | $CH_3$ | $CH_3$ | H | $CH_3$ | $OCH_3$ | |
| $OCH(CH_3)CH=CH_2$ | $CH_3$ | $CH_3$ | H | $CH_3$ | $OCH_3$ | |
| $SO_2N(CH_3)_2$ | $CH_3$ | $CH_3$ | H | $CH_3$ | $OCH_3$ | 95–96° (d) |
| $SO_2N(CH_3)CH(CH_3)_2$ | $CH_3$ | $CH_3$ | H | $CH_3$ | $OCH_3$ | |
| $SO_2N(OCH_3)CH_3$ | $CH_3$ | $CH_3$ | H | $CH_3$ | $OCH_3$ | |
| $CH_2OCH_3$ | $CH_3$ | $CH_3$ | H | $CH_3$ | $OCH_3$ | |
| $CH_2CH_2OCH_3$ | $CH_3$ | $CH_3$ | H | $CH_3$ | $OCH_3$ | |
| F | $CH_3$ | $CH_3$ | H | $CH_3$ | $OCH_3$ | |
| Cl | $CH_3$ | $CH_3$ | H | $CH_3$ | $OCH_3$ | 89–90° C. (d) |
| Br | $CH_3$ | $CH_3$ | H | $CH_3$ | $OCH_3$ | |
| $NO_2$ | $CH_3$ | $CH_3$ | H | $CH_3$ | $OCH_3$ | 172–173° (d) |
| $CF_3$ | $CH_3$ | $CH_3$ | H | $CH_3$ | $OCH_3$ | |
| $CH_3$ | $CH_3$ | $CH_3$ | H | $CH_3$ | $OCH_3$ | |
| $CH_2CH_3$ | $CH_3$ | $CH_3$ | H | $CH_3$ | $OCH_3$ | |
| $CH(CH_3)_2$ | $CH_3$ | $CH_3$ | H | $CH_3$ | $OCH_3$ | |
| $CH_2CH_2CH_2CH_3$ | $CH_3$ | $CH_3$ | H | $CH_3$ | $OCH_3$ | |
| $CO_2CH_3$ | $CH_3$ | $CH_3$ | H | Br | $OCH_3$ | |
| $SCH_3$ | $C_2H_5$ | $CH_3$ | H | $CH_3$ | $OCH_3$ | |
| $SCF_3$ | $C_2H_5$ | $CH_3$ | H | $CH_3$ | $OCH_3$ | |
| $NO_2$ | $CH_3$ | $CH_3$ | 5-$CF_3$ | $CH_3$ | $OCH_3$ | |
| $NO_2$ | $CH_3$ | $CH_3$ | 3-Cl | $CH_3$ | $OCH_3$ | |
| Cl | $CH_3$ | $CH_3$ | 6-$SCH_3$ | $CH_3$ | $OCH_3$ | |
| $CF_3$ | $CH_3$ | $CH_3$ | 5-$OCF_2H$ | $CH_3$ | $OCH_3$ | |
| Cl | $CH_3$ | $CH_3$ | 5-Cl | $CH_3$ | $OCH_3$ | |
| $NO_2$ | $CH_3$ | $CH_3$ | 5-Cl | $CH_3$ | $OCH_3$ | |
| $SO_2N(CH_3)_2$ | $CH_3$ | $CH_3$ | 3-Cl | $CH_3$ | $OCH_3$ | |
| $CO_2CH_3$ | $CH_3$ | $CH_3$ | 5-$CH_3$ | $CH_3$ | $OCH_3$ | |
| Cl | $CH_3$ | $CH_3$ | 3-Br | $CH_3$ | $OCH_3$ | |
| Cl | $CH_3$ | $CH_3$ | 5-Br | $CH_3$ | $OCH_3$ | |
| $NO_2$ | $CH_3$ | $CH_3$ | 6-F | $CH_3$ | $OCH_3$ | |
| Cl | $CH_3$ | $CH_3$ | 6-F | $CH_3$ | $OCH_3$ | |
| Br | $CH_3$ | $CH_3$ | 3-F | $CH_3$ | $OCH_3$ | |
| $NO_2$ | $CH_3$ | $CH_3$ | 5-$SCH_3$ | $CH_3$ | $OCH_3$ | |
| $CO_2CH_3$ | $CH_3$ | $CH_3$ | 3-$OCH_3$ | $CH_3$ | $OCH_3$ | |
| $CH_3$ | $CH_3$ | $CH_3$ | 3-$OCH_3$ | $CH_3$ | $OCH_3$ | |

TABLE I-continued

| R₅ | Rₐ | R_b | R₆ | X | Y | m.p. (°C.) |
|---|---|---|---|---|---|---|
| CO₂CH₃ | C₂H₅ | CH₃ | H | OCH₃ | OCH₃ | |
| CO₂CH₃ | C₂H₅ | C₂H₅ | H | OCH₃ | OCH₃ | |
| NO₂ | C₂H₅ | CH₃ | H | OCH₃ | OCH₃ | |
| SO₂N(CH₃)₂ | C₂H₅ | CH₃ | H | OCH₃ | OCH₃ | |
| CO₂CH₃ | CH₃ | CH₃ | H | OCH₃ | CH₂OCH₃ | |
| CO₂CH₃ | CH₃ | CH₃ | H | OCH₃ | CH(OCH₃)₂ | |
| CO₂CH₃ | CH₃ | CH₃ | H | OCH₃ | CH(OCH₂CH₂O) | |
| NO₂ | C₂H₅ | C₂H₅ | H | OCH₃ | OCH₃ | |
| SO₂N(CH₃)₂ | C₂H₅ | C₂H₅ | H | OCH₃ | OCH₃ | |
| CO₂CH₃ | CH₃ | CH₃ | H | OCH₃ | OCH₃ | |
| CO₂CH₂CH₃ | CH₃ | CH₃ | H | OCH₃ | OCH₃ | |
| CO₂CH₂CH₂CH₃ | CH₃ | CH₃ | H | OCH₃ | OCH₃ | |
| CO₂CH(CH₃)₂ | CH₃ | CH₃ | H | OCH₃ | OCH₃ | 152–154° (d) |
| CO₂CH₂CH₂CH₂CH₃ | CH₃ | CH₃ | H | OCH₃ | OCH₃ | |
| CO₂CH₂CH=CH₂ | CH₃ | CH₃ | H | OCH₃ | OCH₃ | 151–153° (d) |
| CO₂CH₂CH₂OCH₃ | CH₃ | CH₃ | H | OCH₃ | OCH₃ | |
| CO₂CH₂CH₂Cl | CH₃ | CH₃ | H | OCH₃ | OCH₃ | |
| SCH₃ | CH₃ | CH₃ | H | OCH₃ | OCH₃ | |
| SCH₂CH₃ | CH₃ | CH₃ | H | OCH₃ | OCH₃ | |
| SCH(CH₃)₂ | CH₃ | CH₃ | H | OCH₃ | OCH₃ | |
| SCH₂CH=CH₂ | CH₃ | CH₃ | H | OCH₃ | OCH₃ | |
| SCF₃ | CH₃ | CH₃ | H | OCH₃ | OCH₃ | |
| SCF₂H | CH₃ | CH₃ | H | OCH₃ | OCH₃ | |
| SO₂CH₃ | CH₃ | CH₃ | H | OCH₃ | OCH₃ | |
| SO₂CH₂CH₃ | CH₃ | CH₃ | H | OCH₃ | OCH₃ | |
| SO₂CH(CH₃)₂ | CH₃ | CH₃ | H | OCH₃ | OCH₃ | |
| SO₂CH₂CH=CH₂ | CH₃ | CH₃ | H | OCH₃ | OCH₃ | |
| SO₂CF₃ | CH₃ | CH₃ | H | OCH₃ | OCH₃ | |
| SO₂CF₂H | CH₃ | CH₃ | H | OCH₃ | OCH₃ | |
| OSO₂CH₃ | CH₃ | CH₃ | H | OCH₃ | OCH₃ | |
| OSO₂CH₂CH₃ | CH₃ | CH₃ | H | OCH₃ | OCH₃ | |
| OSO₂CH(CH₃)₂ | CH₃ | CH₃ | H | OCH₃ | OCH₃ | |
| OCH₃ | CH₃ | CH₃ | H | OCH₃ | OCH₃ | |
| OCH₂CH₃ | CH₃ | CH₃ | H | OCH₃ | OCH₃ | |
| OCH(CH₃)₂ | CH₃ | CH₃ | H | OCH₃ | OCH₃ | |
| OCH₂CH₂CH₂CH₃ | CH₃ | CH₃ | H | OCH₃ | OCH₃ | |
| OCH₂CH=CH₂ | CH₃ | CH₃ | H | OCH₃ | OCH₃ | |
| OCH₂CH₂CH=CH₂ | CH₃ | CH₃ | H | OCH₃ | OCH₃ | |
| OCH(CH₃)CH=CH₂ | CH₃ | CH₃ | H | OCH₃ | OCH₃ | |
| SO₂N(CH₃)₂ | CH₃ | CH₃ | H | OCH₃ | OCH₃ | 173–175° (d) |
| SO₂N(CH₃)CH(CH₃)₂ | CH₃ | CH₃ | H | OCH₃ | OCH₃ | |
| SO₂N(OCH₃)CH₃ | CH₃ | CH₃ | H | OCH₃ | OCH₃ | |
| CH₂OCH₃ | CH₃ | CH₃ | H | OCH₃ | OCH₃ | |
| CH₂CH₂OCH₃ | CH₃ | CH₃ | H | OCH₃ | OCH₃ | |
| F | CH₃ | CH₃ | H | OCH₃ | OCH₃ | |
| Cl | CH₃ | CH₃ | H | OCH₃ | OCH₃ | |
| Br | CH₃ | CH₃ | H | OCH₃ | OCH₃ | |
| NO₂ | CH₃ | CH₃ | H | OCH₃ | OCH₃ | |
| CF₃ | CH₃ | CH₃ | H | OCH₃ | OCH₃ | |
| CH₃ | CH₃ | CH₃ | H | OCH₃ | OCH₃ | |
| CH₂CH₃ | CH₃ | CH₃ | H | OCH₃ | OCH₃ | |
| CH(CH₃)₂ | CH₃ | CH₃ | H | OCH₃ | OCH₃ | |
| CH₂CH₂CH₂CH₃ | CH₃ | CH₃ | H | OCH₃ | OCH₃ | |
| SO₂N(CH₃)₂ | CH₃ | CH₃ | H | Cl | OCH₃ | |
| SCH₃ | C₂H₅ | CH₃ | H | OCH₃ | OCH₃ | |
| SCF₃ | C₂H₅ | CH₃ | H | OCH₃ | OCH₃ | |
| NO₂ | CH₃ | CH₃ | 5-CF₃ | OCH₃ | OCH₃ | |
| NO₂ | CH₃ | CH₃ | 3-Cl | OCH₃ | OCH₃ | |
| Cl | CH₃ | CH₃ | 6-SCH₃ | OCH₃ | OCH₃ | |
| CF₃ | CH₃ | CH₃ | 5-OCF₂H | OCH₃ | OCH₃ | |
| Cl | CH₃ | CH₃ | 5-Cl | OCH₃ | OCH₃ | |
| NO₂ | CH₃ | CH₃ | 5-Cl | OCH₃ | OCH₃ | |
| SO₂N(CH₃)₂ | CH₃ | CH₃ | 3-Cl | OCH₃ | OCH₃ | |
| CO₂CH₃ | CH₃ | CH₃ | 5-CH₃ | OCH₃ | OCH₃ | |
| Cl | CH₃ | CH₃ | 3-Br | OCH₃ | OCH₃ | |
| Cl | CH₃ | CH₃ | 5-Br | OCH₃ | OCH₃ | |
| NO₂ | CH₃ | CH₃ | 6-F | OCH₃ | OCH₃ | |
| Cl | CH₃ | CH₃ | 6-F | OCH₃ | OCH₃ | |
| Br | CH₃ | CH₃ | 3-F | OCH₃ | OCH₃ | |
| NO₂ | CH₃ | CH₃ | 5-SCH₃ | OCH₃ | OCH₃ | |
| CO₂CH₃ | CH₃ | CH₃ | 3-OCH₃ | OCH₃ | OCH₃ | |

TABLE I-continued

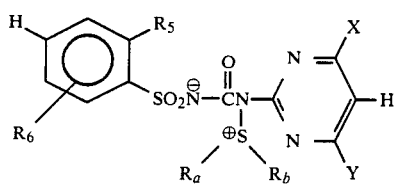

| $R_5$ | $R_a$ | $R_b$ | $R_6$ | X | Y | m.p. (°C.) |
|---|---|---|---|---|---|---|
| CH$_3$ | CH$_3$ | CH$_3$ | 3-OCH$_3$ | OCH$_3$ | OCH$_3$ | |
| CO$_2$CH$_3$ | CH$_3$ | CH$_3$ | H | OCF$_2$H | CH$_3$ | |
| CO$_2$CH$_3$ | CH$_3$ | CH$_3$ | H | CH$_2$F | OCH$_3$ | |
| CO$_2$CH$_3$ | CH$_3$ | CH$_3$ | H | CH$_3$ | C$_2$H$_5$ | |
| CO$_2$CH$_3$ | CH$_3$ | CH$_3$ | H | OCH$_3$ | C$_2$H$_5$ | |
| CO$_2$CH$_3$ | CH$_3$ | CH$_3$ | H | CF$_3$ | OCH$_3$ | |
| CO$_2$CH$_3$ | CH$_3$ | CH$_3$ | H | CF$_3$ | CH$_3$ | |
| CO$_2$CH$_3$ | CH$_3$ | CH$_3$ | H | OC$_2$H$_5$ | CH$_3$ | |
| CO$_2$CH$_3$ | CH$_3$ | CH$_3$ | H | OC$_2$H$_5$ | OCH$_3$ | |
| CO$_2$CH$_3$ | CH$_3$ | CH$_3$ | H | CH$_3$ | OCH$_2$CF$_3$ | |
| CO$_2$CH$_3$ | CH$_3$ | CH$_3$ | H | OCH$_3$ | OCH$_2$CF$_3$ | |
| ![N-N,O,H oxadiazole] | CH$_3$ | CH$_3$ | H | CH$_3$ | CH$_3$ | |
| ![N-N,O,H oxadiazole] | CH$_3$ | CH$_3$ | H | CH$_3$ | OCH$_3$ | |
| ![N-N,O,H oxadiazole] | CH$_3$ | CH$_3$ | H | OCH$_3$ | OCH$_3$ | |
| ![N-N,O,CH3 oxadiazole] | CH$_3$ | CH$_3$ | H | CH$_3$ | CH$_3$ | |
| ![N-N,O,CH3 oxadiazole] | CH$_3$ | CH$_3$ | H | CH$_3$ | OCH$_3$ | |
| ![N-N,O,CH3 oxadiazole] | CH$_3$ | CH$_3$ | H | OCH$_3$ | OCH$_3$ | |
| ![N-O isoxazole] | CH$_3$ | CH$_3$ | H | CH$_3$ | CH$_3$ | |
| ![N-O isoxazole] | CH$_3$ | CH$_3$ | H | CH$_3$ | OCH$_3$ | |
| ![N-O isoxazole] | CH$_3$ | CH$_3$ | H | OCH$_3$ | OCH$_3$ | |
| ![O-N isoxazole] | CH$_3$ | CH$_3$ | H | CH$_3$ | CH$_3$ | |
| ![O-N isoxazole] | CH$_3$ | CH$_3$ | H | CH$_3$ | OCH$_3$ | |

TABLE I-continued

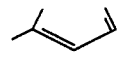

| R5 | Ra | Rb | R6 | X | Y | m.p. (°C.) |
|---|---|---|---|---|---|---|
| 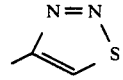 | CH3 | CH3 | H | OCH3 | OCH3 | |
| 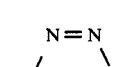 | CH3 | CH3 | H | CH3 | CH3 | |
| 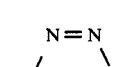 | CH3 | CH3 | H | CH3 | OCH3 | |
| 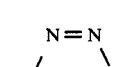 | CH3 | CH3 | H | OCH3 | OCH3 | |
| CO2CH3 | CH3 | CH3 | H | OCH3 | N(CH3)2 | |
| CO2CH3 | CH3 | CH3 | H | OCH3 | SCH3 | |
| CO2CH3 | CH3 | CH3 | H | OCH3 | OCH2CH=CH2 | |
| CO2CH3 | CH3 | CH3 | H | OCH3 | OCH2C≡CH | |
| CO2CH3 | CH3 | CH3 | H | OCH3 | CH2SCH3 | |
| CO2CH3 | CH3 | CH3 | H | OCH3 | SCF2H | |

TABLE II

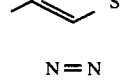

| R5 | Ra | Rb | R6 | X | Y | m.p. (°C.) |
|---|---|---|---|---|---|---|
| CO2CH3 | CH3 | CH3 | H | CH3 | CH3 | |
| CO2CH2CH3 | CH3 | CH3 | H | CH3 | CH3 | |
| CO2CH2CH2CH3 | CH3 | CH3 | H | CH3 | CH3 | |
| CO2CH3 | C2H5 | C2H5 | H | CH3 | CH3 | |
| CO2CH3 | C2H5 | CH3 | H | CH3 | CH3 | |
| CO2CH2CH=CH2 | CH3 | CH3 | H | CH3 | CH3 | |
| CO2CH2CH2OCH3 | CH3 | CH3 | H | CH3 | CH3 | |
| CO2CH2CH2Cl | CH3 | CH3 | H | CH3 | CH3 | |
| SCH3 | CH3 | CH3 | H | CH3 | CH3 | |
| SCH2CH3 | CH3 | CH3 | H | CH3 | CH3 | |
| SCH(CH3)2 | CH3 | CH3 | H | CH3 | CH3 | |
| SCH2CH=CH2 | CH3 | CH3 | H | CH3 | CH3 | |
| SCF3 | CH3 | CH3 | H | CH3 | CH3 | |
| SCF2H | CH3 | CH3 | H | CH3 | CH3 | |
| SO2CH3 | CH3 | CH3 | H | CH3 | CH3 | |
| SO2CH3 | C2H5 | C2H5 | H | CH3 | CH3 | |
| SO2CH3 | C2H5 | CH3 | H | CH3 | CH3 | |
| SO2CH2CH=CH2 | CH3 | CH3 | H | CH3 | CH3 | |
| SO2CF3 | CH3 | CH3 | H | CH3 | CH3 | |
| SO2CF2H | CH3 | CH3 | H | CH3 | CH3 | |
| OSO2CH3 | CH3 | CH3 | H | CH3 | CH3 | |
| OSO2CH2CH3 | CH3 | CH3 | H | CH3 | CH3 | |
| OSO2CH(CH3)2 | CH3 | CH3 | H | CH3 | CH3 | |
| OCH3 | CH3 | CH3 | H | CH3 | CH3 | |
| OCH2CH3 | CH3 | CH3 | H | CH3 | CH3 | |
| OCH2CH2CH3 | CH3 | CH3 | H | CH3 | CH3 | |
| OCH(CH3)CH2CH3 | CH3 | CH3 | H | CH3 | CH3 | |
| OCH2CH=CH2 | CH3 | CH3 | H | CH3 | CH3 | |
| OCH2CH2CH=CH2 | CH3 | CH3 | H | CH3 | CH3 | |

TABLE II-continued

| R5 | Rₐ | R_b | R6 | X | Y | m.p. (°C.) |
|---|---|---|---|---|---|---|
| OCH(CH₃)CH=CH₂ | CH₃ | CH₃ | H | CH₃ | CH₃ | |
| SO₂N(CH₃)₂ | CH₃ | CH₃ | H | CH₃ | CH₃ | |
| SO₂N(CH₃)CH(CH₃)₂ | CH₃ | CH₃ | H | CH₃ | CH₃ | |
| SO₂N(OCH₃)CH₃ | CH₃ | CH₃ | H | CH₃ | CH₃ | |
| CH₂OCH₃ | CH₃ | CH₃ | H | CH₃ | CH₃ | |
| CH₂CH₂OCH₃ | CH₃ | CH₃ | H | CH₃ | CH₃ | |
| F | CH₃ | CH₃ | H | CH₃ | CH₃ | |
| Cl | CH₃ | CH₃ | H | CH₃ | CH₃ | |
| Br | CH₃ | CH₃ | H | CH₃ | CH₃ | |
| NO₂ | CH₃ | CH₃ | H | CH₃ | CH₃ | |
| CF₃ | CH₃ | CH₃ | H | CH₃ | CH₃ | |
| CH₃ | CH₃ | CH₃ | H | CH₃ | CH₃ | |
| CH₂CH₃ | CH₃ | CH₃ | H | CH₃ | CH₃ | |
| CH(CH₃)₂ | CH₃ | CH₃ | H | CH₃ | CH₃ | |
| CH₂CH₂CH₂CH₃ | CH₃ | CH₃ | H | CH₃ | CH₃ | |
| CO₂CH₂CH₂CH₃ | CH₃ | CH₃ | H | CH₃ | CH₃ | |
| SO₂CH₂CH₃ | C₂H₅ | C₂H₅ | H | CH₃ | CH₃ | |
| CH₂OCH₃ | CH₃ | CH₃ | H | CH₃ | CH₃ | |
| CH₂CH₂OCH₃ | CH₃ | CH₃ | H | CH₃ | CH₃ | |
| NO₂ | CH₃ | CH₃ | 5-CF₃ | CH₃ | CH₃ | |
| NO₂ | CH₃ | CH₃ | 3-Cl | CH₃ | CH₃ | |
| Cl | CH₃ | CH₃ | 6-SCH₃ | CH₃ | CH₃ | |
| CF₃ | CH₃ | CH₃ | 5-OCF₂H | CH₃ | CH₃ | |
| Cl | CH₃ | CH₃ | 5-Cl | CH₃ | CH₃ | |
| NO₂ | CH₃ | CH₃ | 5-Cl | CH₃ | CH₃ | |
| SO₂N(CH₃)₂ | C₂H₅ | C₂H₅ | 3-Cl | CH₃ | CH₃ | |
| CO₂CH₃ | CH₃ | CH₃ | 5-CH₃ | CH₃ | CH₃ | |
| Cl | CH₃ | CH₃ | 3-Br | CH₃ | CH₃ | |
| Cl | CH₃ | CH₃ | 5-Br | CH₃ | CH₃ | |
| NO₂ | CH₃ | CH₃ | 6-F | CH₃ | CH₃ | |
| Cl | CH₃ | CH₃ | 6-F | CH₃ | CH₃ | |
| Br | CH₃ | CH₃ | 3-F | CH₃ | CH₃ | |
| NO₂ | C₂H₅ | C₂H₅ | 5-SCH₃ | CH₃ | CH₃ | |
| CO₂CH₃ | CH₃ | CH₃ | 3-OCH₃ | CH₃ | CH₃ | |
| CH₃ | CH₃ | CH₃ | 3-OCH₃ | CH₃ | CH₃ | |
| CO₂CH₃ | C₂H₅ | CH₃ | H | CH₃ | OCH₃ | |
| CO₂CH₃ | C₂H₅ | C₂H₅ | H | CH₃ | OCH₃ | |
| NO₂ | C₂H₅ | CH₃ | H | CH₃ | OCH₃ | |
| SO₂N(CH₃)₂ | C₂H₅ | CH₃ | H | CH₃ | OCH₃ | |
| CO₂CH₃ | CH₃ | CH₃ | H | CH₃ | CH₂OCH₃ | |
| CO₂CH₃ | CH₃ | CH₃ | H | CH₃ | CH(OCH₃)₂ | |
| CO₂CH₃ | CH₃ | CH₃ | H | CH₃ | CH(OCH₂CH₂O) | |
| NO₂ | C₂H₅ | C₂H₅ | H | CH₃ | OCH₃ | |
| SO₂N(CH₃)₂ | C₂H₅ | C₂H₅ | H | CH₃ | OCH₃ | |
| CO₂CH₃ | CH₃ | CH₃ | H | CH₃ | OCH₃ | |
| CO₂CH₂CH₃ | CH₃ | CH₃ | H | CH₃ | OCH₃ | |
| CO₂CH₂CH₂CH₃ | CH₃ | CH₃ | H | CH₃ | OCH₃ | |
| CO₂CH(CH₃)₂ | CH₃ | CH₃ | H | CH₃ | OCH₃ | 89-91° (d) |
| CO₂CH₂CH₂CH₂CH₃ | CH₃ | CH₃ | H | CH₃ | OCH₃ | |
| CO₂CH₂CH=CH₂ | CH₃ | CH₃ | H | CH₃ | OCH₃ | |
| CO₂CH₂CH₂OCH₃ | CH₃ | CH₃ | H | CH₃ | OCH₃ | |
| CO₂CH₂CH₂Cl | CH₃ | CH₃ | H | CH₃ | OCH₃ | |
| SCH₃ | CH₃ | CH₃ | H | CH₃ | OCH₃ | |
| SCH₂CH₃ | CH₃ | CH₃ | H | CH₃ | OCH₃ | |
| SCH(CH₃)₂ | CH₃ | CH₃ | H | CH₃ | OCH₃ | |
| SCH₂CH=CH₂ | CH₃ | CH₃ | H | CH₃ | OCH₃ | |
| SCF₃ | CH₃ | CH₃ | H | CH₃ | OCH₃ | |
| SCF₂H | CH₃ | CH₃ | H | CH₃ | OCH₃ | |
| SO₂CH₃ | CH₃ | CH₃ | H | CH₃ | OCH₃ | |
| SO₂CH₂CH₃ | CH₃ | CH₃ | H | CH₃ | OCH₃ | |
| SO₂CH(CH₃)₂ | CH₃ | CH₃ | H | CH₃ | OCH₃ | |
| SO₂CH₂CH=CH₂ | CH₃ | CH₃ | H | CH₃ | OCH₃ | |
| SO₂CF₃ | CH₃ | CH₃ | H | CH₃ | OCH₃ | |
| SO₂CF₂H | CH₃ | CH₃ | H | CH₃ | OCH₃ | |
| OSO₂CH₃ | CH₃ | CH₃ | H | CH₃ | OCH₃ | |
| OSO₂CH₂CH₃ | CH₃ | CH₃ | H | CH₃ | OCH₃ | |
| OSO₂CH(CH₃)₂ | CH₃ | CH₃ | H | CH₃ | OCH₃ | |
| OCH₃ | CH₃ | CH₃ | H | CH₃ | OCH₃ | |
| OCH₂CH₃ | CH₃ | CH₃ | H | CH₃ | OCH₃ | |
| OCH(CH₃)₂ | CH₃ | CH₃ | H | CH₃ | OCH₃ | |
| OCH₂CH₂CH₂CH₃ | CH₃ | CH₃ | H | CH₃ | OCH₃ | |

TABLE II-continued

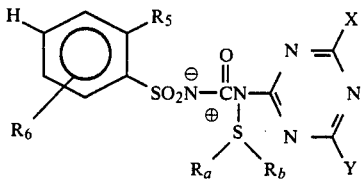

| R5 | Ra | Rb | R6 | X | Y | m.p. (°C.) |
|---|---|---|---|---|---|---|
| OCH2CH=CH2 | CH3 | CH3 | H | CH3 | OCH3 | |
| OCH2CH2CH=CH2 | CH3 | CH3 | H | CH3 | OCH3 | |
| OCH(CH3)CH=CH2 | CH3 | CH3 | H | CH3 | OCH3 | |
| SO2N(CH3)2 | CH3 | CH3 | H | CH3 | OCH3 | |
| SO2N(CH3)CH(CH3)2 | CH3 | CH3 | H | CH3 | OCH3 | |
| SO2N(OCH3)CH3 | CH3 | CH3 | H | CH3 | OCH3 | |
| CH2OCH3 | CH3 | CH3 | H | CH3 | OCH3 | |
| CH2CH2OCH3 | CH3 | CH3 | H | CH3 | OCH3 | |
| F | CH3 | CH3 | H | CH3 | OCH3 | |
| Cl | CH3 | CH3 | H | CH3 | OCH3 | |
| Br | CH3 | CH3 | H | CH3 | OCH3 | |
| NO2 | CH3 | CH3 | H | CH3 | OCH3 | |
| CF3 | CH3 | CH3 | H | CH3 | OCH3 | |
| CH3 | CH3 | CH3 | H | CH3 | OCH3 | |
| CH2CH3 | CH3 | CH3 | H | CH3 | OCH3 | |
| CH(CH3)2 | CH3 | CH3 | H | CH3 | OCH3 | |
| CH2CH2CH2CH3 | CH3 | CH3 | H | CH3 | OCH3 | |
| SCH3 | C2H5 | CH3 | H | CH3 | OCH3 | |
| SCF3 | C2H5 | CH3 | H | CH3 | OCH3 | |
| NO2 | CH3 | CH3 | 5-CF3 | CH3 | OCH3 | |
| NO2 | CH3 | CH3 | 3-Cl | CH3 | OCH3 | |
| Cl | CH3 | CH3 | 6-SCH3 | CH3 | OCH3 | |
| CF3 | CH3 | CH3 | 5-OCF2H | CH3 | OCH3 | |
| Cl | CH3 | CH3 | 5-Cl | CH3 | OCH3 | |
| NO2 | CH3 | CH3 | 5-Cl | CH3 | OCH3 | |
| SO2N(CH3)2 | CH3 | CH3 | 3-Cl | CH3 | OCH3 | |
| CO2CH3 | CH3 | CH3 | 5-CH3 | CH3 | OCH3 | |
| Cl | CH3 | CH3 | 3-Br | CH3 | OCH3 | |
| Cl | CH3 | CH3 | 5-Br | CH3 | OCH3 | |
| NO2 | CH3 | CH3 | 6-F | CH3 | OCH3 | |
| Cl | CH3 | CH3 | 6-F | CH3 | OCH3 | |
| Br | CH3 | CH3 | 3-F | CH3 | OCH3 | |
| NO2 | CH3 | CH3 | 5-SCH3 | CH3 | OCH3 | |
| CO2CH3 | CH3 | CH3 | 3-OCH3 | CH3 | OCH3 | |
| CH3 | CH3 | CH3 | 3-OCH3 | CH3 | OCH3 | |
| CO2CH3 | C2H5 | CH3 | H | OCH3 | OCH3 | |
| CO2CH3 | C2H5 | C2H5 | H | OCH3 | OCH3 | |
| NO2 | C2H5 | CH3 | H | OCH3 | OCH3 | |
| SO2N(CH3)2 | C2H5 | CH3 | H | OCH3 | OCH3 | |
| CO2CH3 | CH3 | CH3 | H | OCF2H | OCH3 | |
| CO2CH3 | CH3 | CH3 | H | CF3 | OCH3 | |
| CO2CH3 | CH3 | CH3 | H | CH2F | OCH3 | |
| NO2 | C2H5 | C2H5 | H | OCH3 | OCH3 | |
| SO2N(CH3)2 | C2H5 | C2H5 | H | OCH3 | OCH3 | |
| CO2CH3 | CH3 | CH3 | H | OCH3 | OCH3 | 88-90° (d) |
| CO2CH2CH3 | CH3 | CH3 | H | OCH3 | OCH3 | |
| CO2CH2CH2CH3 | CH3 | CH3 | H | OCH3 | OCH3 | |
| CO2CH(CH3)2 | CH3 | CH3 | H | OCH3 | OCH3 | |
| CO2CH2CH2CH2CH3 | CH3 | CH3 | H | OCH3 | OCH3 | |
| CO2CH2CH=CH2 | CH3 | CH3 | H | OCH3 | OCH3 | |
| CO2CH2CH2OCH3 | CH3 | CH3 | H | OCH3 | OCH3 | |
| CO2CH2CH2Cl | CH3 | CH3 | H | OCH3 | OCH3 | |
| SCH3 | CH3 | CH3 | H | OCH3 | OCH3 | |
| SCH2CH3 | CH3 | CH3 | H | OCH3 | OCH3 | |
| SCH(CH3)2 | CH3 | CH3 | H | OCH3 | OCH3 | |
| SCH2CH=CH2 | CH3 | CH3 | H | OCH3 | OCH3 | |
| SCF3 | CH3 | CH3 | H | OCH3 | OCH3 | |
| SCF2H | CH3 | CH3 | H | OCH3 | OCH3 | |
| SO2CH3 | CH3 | CH3 | H | OCH3 | OCH3 | |
| SO2CH2CH3 | CH3 | CH3 | H | OCH3 | OCH3 | |
| SO2CH(CH3)2 | CH3 | CH3 | H | OCH3 | OCH3 | |
| SO2CH2CH=CH2 | CH3 | CH3 | H | OCH3 | OCH3 | |
| SO2CF3 | CH3 | CH3 | H | OCH3 | OCH3 | |
| SO2CF2H | CH3 | CH3 | H | OCH3 | OCH3 | |
| OSO2CH3 | CH3 | CH3 | H | OCH3 | OCH3 | |
| OSO2CH2CH3 | CH3 | CH3 | H | OCH3 | OCH3 | |
| OSO2CH(CH3)2 | CH3 | CH3 | H | OCH3 | OCH3 | |
| OCH3 | CH3 | CH3 | H | OCH3 | OCH3 | |
| OCH2CH3 | CH3 | CH3 | H | OCH3 | OCH3 | |
| OCH(CH3)2 | CH3 | CH3 | H | OCH3 | OCH3 | |
| OCH2CH2CH2CH3 | CH3 | CH3 | H | OCH3 | OCH3 | |

TABLE II-continued

| R₅ | Rₐ | R_b | R₆ | X | Y | m.p. (°C.) |
|---|---|---|---|---|---|---|
| OCH₂CH=CH₂ | CH₃ | CH₃ | H | OCH₃ | OCH₃ | |
| OCH₂CH₂CH=CH₂ | CH₃ | CH₃ | H | OCH₃ | OCH₃ | |
| OCH(CH₃)CH=CH₂ | CH₃ | CH₃ | H | OCH₃ | OCH₃ | |
| SO₂N(CH₃)₂ | CH₃ | CH₃ | H | OCH₃ | OCH₃ | |
| SO₂N(CH₃)CH(CH₃)₂ | CH₃ | CH₃ | H | OCH₃ | OCH₃ | |
| SO₂N(OCH₃)CH₃ | CH₃ | CH₃ | H | OCH₃ | OCH₃ | |
| CH₂OCH₃ | CH₃ | CH₃ | H | OCH₃ | OCH₃ | |
| CH₂CH₂OCH₃ | CH₃ | CH₃ | H | OCH₃ | OCH₃ | |
| F | CH₃ | CH₃ | H | OCH₃ | OCH₃ | |
| Cl | CH₃ | CH₃ | H | OCH₃ | OCH₃ | 98–99° (d) |
| Br | CH₃ | CH₃ | H | OCH₃ | OCH₃ | |
| NO₂ | CH₃ | CH₃ | H | OCH₃ | OCH₃ | 125–127° (d) |
| CF₃ | CH₃ | CH₃ | H | OCH₃ | OCH₃ | |
| CH₃ | CH₃ | CH₃ | H | OCH₃ | OCH₃ | |
| CH₂CH₃ | CH₃ | CH₃ | H | OCH₃ | OCH₃ | |
| CH(CH₃)₂ | CH₃ | CH₃ | H | OCH₃ | OCH₃ | |
| CH₂CH₂CH₂CH₃ | CH₃ | CH₃ | H | OCH₃ | OCH₃ | |
| SCH₃ | C₂H₅ | CH₃ | H | OCH₃ | OCH₃ | |
| SCF₃ | C₂H₅ | CH₃ | H | OCH₃ | OCH₃ | |
| NO₂ | CH₃ | CH₃ | 5-CF₃ | OCH₃ | OCH₃ | |
| NO₂ | CH₃ | CH₃ | 3-Cl | OCH₃ | OCH₃ | |
| Cl | CH₃ | CH₃ | 6-SCH₃ | OCH₃ | OCH₃ | |
| CF₃ | CH₃ | CH₃ | 5-OCF₂H | OCH₃ | OCH₃ | |
| Cl | CH₃ | CH₃ | 5-Cl | OCH₃ | OCH₃ | |
| NO₂ | CH₃ | CH₃ | 5-Cl | OCH₃ | OCH₃ | |
| SO₂N(CH₃)₂ | CH₃ | CH₃ | 3-Cl | OCH₃ | OCH₃ | |
| CO₂CH₃ | CH₃ | CH₃ | 5-CH₃ | OCH₃ | OCH₃ | |
| Cl | CH₃ | CH₃ | 3-Br | OCH₃ | OCH₃ | |
| Cl | CH₃ | CH₃ | 5-Br | OCH₃ | OCH₃ | |
| NO₂ | CH₃ | CH₃ | 6-F | OCH₃ | OCH₃ | |
| Cl | CH₃ | CH₃ | 6-F | OCH₃ | OCH₃ | |
| Br | CH₃ | CH₃ | 3-F | OCH₃ | OCH₃ | |
| NO₂ | CH₃ | CH₃ | 5-SCH₃ | OCH₃ | OCH₃ | |
| CO₂CH₃ | CH₃ | CH₃ | 3-OCH₃ | OCH₃ | OCH₃ | |
| CH₃ | CH₃ | CH₃ | 3-OCH₃ | OCH₃ | OCH₃ | |
| CO₂CH₃ | CH₃ | CH₃ | H | CH₃ | H | |
| CO₂CH₃ | CH₃ | CH₃ | H | OCH₃ | H | |
| CO₂CH₃ | CH₃ | CH₃ | H | CH₃ | C₂H₅ | |
| CO₂CH₃ | CH₃ | CH₃ | H | OCH₃ | C₂H₅ | |
| CO₂CH₃ | CH₃ | CH₃ | H | CF₃ | OCH₃ | |
| CO₂CH₃ | CH₃ | CH₃ | H | CF₃ | CH₃ | |
| CO₂CH₃ | CH₃ | CH₃ | H | OC₂H₅ | N(CH₃)₂ | |
| CO₂CH₃ | CH₃ | CH₃ | H | OC₂H₅ | CH₃ | |
| CO₂CH₃ | CH₃ | CH₃ | H | CH₃ | OCH₂CF₃ | |
| CO₂CH₃ | CH₃ | CH₃ | H | OCH₃ | OCH₂CF₃ | |
| 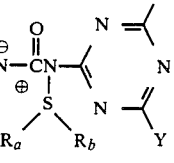 | CH₃ | CH₃ | H | CH₃ | CH₃ | |
|  | CH₃ | CH₃ | H | CH₃ | OCH₃ | |
|  | CH₃ | CH₃ | H | OCH₃ | OCH₃ | |
|  | CH₃ | CH₃ | H | CH₃ | CH₃ | |
|  | CH₃ | CH₃ | H | CH₃ | OCH₃ | |

TABLE II-continued
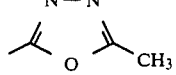
| R5 | Ra | Rb | R6 | X | Y | m.p. (°C.) |
|---|---|---|---|---|---|---|
| 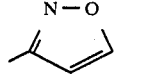 | CH3 | CH3 | H | OCH3 | OCH3 | |
| 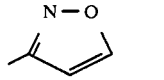 | CH3 | CH3 | H | CH3 | CH3 | |
| 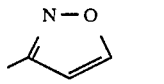 | CH3 | CH3 | H | CH3 | OCH3 | |
| 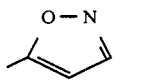 | CH3 | CH3 | H | OCH3 | OCH3 | |
| 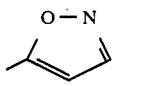 | CH3 | CH3 | H | CH3 | CH3 | |
| 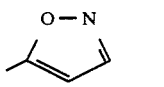 | CH3 | CH3 | H | CH3 | OCH3 | |
| 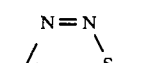 | CH3 | CH3 | H | OCH3 | OCH3 | |
| 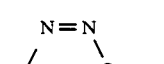 | CH3 | CH3 | H | CH3 | CH3 | |
| 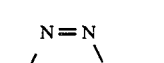 | CH3 | CH3 | H | CH3 | OCH3 | |
| 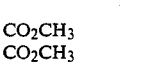 | CH3 | CH3 | H | OCH3 | OCH3 | |
| CO2CH3 | CH3 | CH3 | H | CH3 | OCH2CH=CH2 | |
| CO2CH3 | CH3 | CH3 | H | CH3 | SCH3 | |
| CO2CH3 | CH3 | CH3 | H | CH3 | OCH2C≡CH | |
| CO2CH3 | CH3 | CH3 | H | CH3 | CH2SCH3 | |
| CO2CH3 | CH3 | CH3 | H | CH3 | SCF2H | |

TABLE III

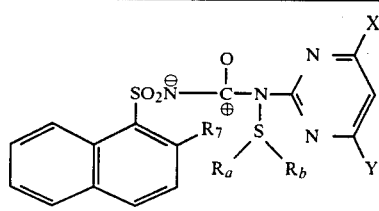

| R7 | Ra | Rb | X | Y | m.p. (°C.) |
|---|---|---|---|---|---|
| H | CH3 | CH3 | CH3 | CH3 | |
| CH3 | CH3 | CH3 | CH3 | CH3 | |
| F | CH3 | CH3 | CH3 | CH3 | |
| Br | CH3 | CH3 | CH3 | CH3 | |
| OCH3 | CH3 | CH3 | CH3 | CH3 | |
| SCH3 | CH3 | CH3 | CH3 | CH3 | |
| Cl | CH3 | CH3 | CH3 | CH3 | |
| OSO2CH3 | CH3 | CH3 | CH3 | CH3 | |
| SO2CH3 | CH3 | CH3 | CH3 | CH3 | |
| H | CH3 | CH3 | CH3 | OCH3 | |
| CH3 | CH3 | CH3 | CH3 | OCH3 | |
| F | CH3 | CH3 | CH3 | OCH3 | |
| Br | CH3 | CH3 | CH3 | OCH3 | |
| OCH3 | CH3 | CH3 | CH3 | OCH3 | |
| SCH3 | CH3 | CH3 | CH3 | OCH3 | |
| Cl | CH3 | CH3 | CH3 | OCH3 | |
| OSO2CH3 | CH3 | CH3 | CH3 | OCH3 | |
| SO2CH3 | CH3 | CH3 | CH3 | OCH3 | |
| OCH3 | C2H5 | C2H5 | CH3 | CH3 | |
| CH3 | C2H5 | CH3 | CH3 | CH3 | |
| F | C2H5 | C2H5 | CH3 | OCH3 | |
| Br | C2H5 | CH3 | CH3 | CH3 | |
| OCH3 | C2H5 | CH3 | OCH3 | OCH3 | |
| SMe | C2H5 | C2H5 | CH3 | OCH3 | |
| Cl | C2H5 | C2H5 | CH3 | CH3 | |
| OSO2CH3 | C2H5 | C2H5 | CH3 | CH3 | |
| SO2CH3 | C2H5 | C2H5 | CH3 | OCH3 | |
| H | CH3 | CH3 | OCH3 | OCH3 | |
| CH3 | CH3 | CH3 | OCH3 | OCH3 | |
| F | CH3 | CH3 | OCH3 | OCH3 | |
| Br | CH3 | CH3 | OCH3 | OCH3 | |
| OCH3 | CH3 | CH3 | OCH3 | OCH3 | |
| SCH3 | CH3 | CH3 | OCH3 | OCH3 | |
| Cl | CH3 | CH3 | OCH3 | OCH3 | |
| OSO2CH3 | CH3 | CH3 | OCH3 | OCH3 | |
| SO2CH3 | CH3 | CH3 | OCH3 | OCH3 | |
| Cl | CH3 | CH3 | Cl | OCH3 | |
| Cl | CH3 | CH3 | Cl | OC2H5 | |
| Cl | CH3 | CH3 | F | OCH3 | |
| Cl | CH3 | CH3 | Br | OCH3 | |
| Cl | CH3 | CH3 | OCF2H | CH3 | |
| Cl | CH3 | CH3 | CH2F | OCH3 | |
| Cl | CH3 | CH3 | CH3 | CH2OCH3 | |
| Cl | CH3 | CH3 | OCH3 | CH2OCH3 | |
| Cl | CH3 | CH3 | CH3 | CH(OCH3)2 | |
| Cl | CH3 | CH3 | OCH3 | CH(OCH3)2 | |
| Cl | CH3 | CH3 | CH3 | CH(OCH2CH2O) | |
| Cl | CH3 | CH3 | OCH3 | CH(OCH2CH2O) | |
| Cl | CH3 | CH3 | CF3 | CH3 | |
| Cl | CH3 | CH3 | CF3 | OCH3 | |
| Cl | CH3 | CH3 | OC2H5 | CH3 | |
| Cl | CH3 | CH3 | OC2H5 | OCH3 | |
| Cl | CH3 | CH3 | CH3 | N(CH3)2 | |
| Cl | CH3 | CH3 | OCH3 | SCH3 | |

TABLE IV

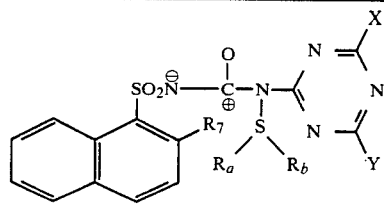

| R7 | Ra | Rb | X | Y | m.p.(°C.) |
|---|---|---|---|---|---|
| H | CH3 | CH3 | CH3 | CH3 | |
| CH3 | CH3 | CH3 | CH3 | CH3 | |
| F | CH3 | CH3 | CH3 | CH3 | |
| Br | CH3 | CH3 | CH3 | CH3 | |
| OCH3 | CH3 | CH3 | CH3 | CH3 | |
| SCH3 | CH3 | CH3 | CH3 | CH3 | |
| Cl | CH3 | CH3 | CH3 | CH3 | |
| OSO2CH3 | CH3 | CH3 | CH3 | CH3 | |
| SO2CH3 | CH3 | CH3 | CH3 | CH3 | |
| H | CH3 | CH3 | CH3 | OCH3 | |
| CH3 | CH3 | CH3 | CH3 | OCH3 | |
| F | CH3 | CH3 | CH3 | OCH3 | |
| Br | CH3 | CH3 | CH3 | OCH3 | |
| OCH3 | CH3 | CH3 | CH3 | OCH3 | |
| SCH3 | CH3 | CH3 | CH3 | OCH3 | |
| Cl | CH3 | CH3 | CH3 | OCH3 | |
| OSO2CH3 | CH3 | CH3 | CH3 | OCH3 | |
| SO2CH3 | CH3 | CH3 | CH3 | OCH3 | |
| OCH3 | C2H5 | C2H5 | CH3 | CH3 | |
| CH3 | C2H5 | CH3 | CH3 | CH3 | |
| F | C2H5 | C2H5 | CH3 | OCH3 | |
| Br | C2H5 | CH3 | CH3 | CH3 | |
| OCH3 | C2H5 | CH3 | OCH3 | OCH3 | |
| SCH3 | C2H5 | C2H5 | CH3 | OCH3 | |
| Cl | C2H5 | C2H5 | CH3 | CH3 | |
| OSO2CH3 | C2H5 | C2H5 | CH3 | CH3 | |
| SO2CH3 | C2H5 | C2H5 | CH3 | OCH3 | |
| H | CH3 | CH3 | OCH3 | OCH3 | |
| CH3 | CH3 | CH3 | OCH3 | OCH3 | |
| F | CH3 | CH3 | OCH3 | OCH3 | |
| Br | CH3 | CH3 | OCH3 | OCH3 | |
| OCH3 | CH3 | CH3 | OCH3 | OCH3 | |
| SCH3 | CH3 | CH3 | OCH3 | OCH3 | |
| Cl | CH3 | CH3 | OCH3 | OCH3 | |
| OSO2CH3 | CH3 | CH3 | OCH3 | OCH3 | |
| SO2CH3 | CH3 | CH3 | OCH3 | OCH3 | |
| Cl | CH3 | CH3 | CH3 | H | |
| Cl | CH3 | CH3 | OCH3 | H | |
| Cl | CH3 | CH3 | CH3 | C2H5 | |
| Cl | CH3 | CH3 | OCH3 | C2H5 | |
| Cl | CH3 | CH3 | CH3 | CH2OCH3 | |
| Cl | CH3 | CH3 | OCH3 | CH2OCH3 | |
| Cl | CH3 | CH3 | CH3 | CH(OCH3)2 | |
| Cl | CH3 | CH3 | OCH3 | CH(OCH3)2 | |
| Cl | CH3 | CH3 | CH3 | CH(OCH2CH2O) | |
| Cl | CH3 | CH3 | OCH3 | CH(OCH2CH2O) | |
| Cl | CH3 | CH3 | CF3 | CH3 | |
| Cl | CH3 | CH3 | CF3 | OCH3 | |
| Cl | CH3 | CH3 | OC2H5 | CH3 | |
| Cl | CH3 | CH3 | OC2H5 | OCH3 | |
| Cl | CH3 | CH3 | CH3 | OCH2CF3 | |
| Cl | CH3 | CH3 | OCH3 | OCH2CF3 | |

TABLE V

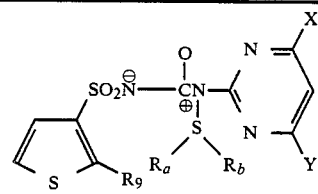

| R9 | Ra | Rb | X | Y | m.p. (°C.) |
|---|---|---|---|---|---|
| F | CH3 | CH3 | CH3 | CH3 | |
| CH3 | CH3 | CH3 | CH3 | CH3 | |

TABLE V-continued

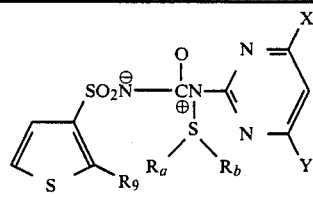

| $R_9$ | $R_a$ | $R_b$ | X | Y | m.p. (°C.) |
|---|---|---|---|---|---|
| Cl | CH₃ | CH₃ | CH₃ | CH₃ | |
| Br | CH₃ | CH₃ | CH₃ | CH₃ | |
| NO₂ | CH₃ | CH₃ | CH₃ | CH₃ | |
| SO₂CH₃ | CH₃ | CH₃ | CH₃ | CH₃ | |
| SO₂N(CH₃)₂ | CH₃ | CH₃ | CH₃ | CH₃ | |
| CO₂CH₃ | CH₃ | CH₃ | CH₃ | CH₃ | |
| F | CH₃ | CH₃ | CH₃ | OCH₃ | |
| CH₃ | CH₃ | CH₃ | CH₃ | OCH₃ | |
| Cl | CH₃ | CH₃ | CH₃ | OCH₃ | |
| Br | CH₃ | CH₃ | CH₃ | OCH₃ | |
| NO₂ | CH₃ | CH₃ | CH₃ | OCH₃ | |
| SO₂CH₃ | CH₃ | CH₃ | CH₃ | OCH₃ | |
| SO₂N(CH₃)₂ | CH₃ | CH₃ | CH₃ | OCH₃ | |
| CO₂CH₃ | CH₃ | CH₃ | CH₃ | OCH₃ | |
| CO₂CH₃ | C₂H₅ | C₂H₅ | OCH₃ | OCH₃ | |
| CO₂CH₃ | C₂H₅ | CH₃ | CH₃ | CH₃ | |
| Cl | C₂H₅ | CH₃ | OCH₃ | OCH₃ | |
| Br | C₂H₅ | C₂H₅ | OCH₃ | OCH₃ | |
| NO₂ | C₂H₅ | C₂H₅ | CH₃ | OCH₃ | |
| SO₂CH₃ | C₂H₅ | C₂H₅ | CH₃ | CH₃ | |
| SO₂N(CH₃)₂ | C₂H₅ | C₂H₅ | CH₃ | CH₃ | |
| CO₂CH₃ | C₂H₅ | C₂H₅ | CH₃ | CH₃ | |
| F | CH₃ | CH₃ | OCH₃ | OCH₃ | |
| CH₃ | CH₃ | CH₃ | OCH₃ | OCH₃ | |
| Cl | CH₃ | CH₃ | OCH₃ | OCH₃ | |
| Br | CH₃ | CH₃ | OCH₃ | OCH₃ | |
| NO₂ | CH₃ | CH₃ | OCH₃ | OCH₃ | |
| SO₂CH₃ | CH₃ | CH₃ | OCH₃ | OCH₃ | |
| SO₂N(CH₃)₂ | CH₃ | CH₃ | OCH₃ | OCH₃ | |
| CO₂CH₃ | CH₃ | CH₃ | OCH₃ | OCH₃ | 125–127° (d) |
| CO₂CH₃ | CH₃ | CH₃ | Cl | OCH₃ | |
| CO₂CH₃ | CH₃ | CH₃ | F | OCH₃ | |
| CO₂CH₃ | CH₃ | CH₃ | OCF₂H | CH₃ | |
| CO₂CH₃ | CH₃ | CH₃ | Br | OCH₃ | |
| CO₂CH₃ | CH₃ | CH₃ | CH₃ | C₂H₅ | |
| CO₂CH₃ | CH₃ | CH₃ | OCH₃ | C₂H₅ | |
| CO₂CH₃ | CH₃ | CH₃ | CH₃ | CH₂OCH₃ | |
| CO₂CH₃ | CH₃ | CH₃ | OCH₃ | CH₂OCH₃ | |
| CO₂CH₃ | CH₃ | CH₃ | CH₃ | CH(OCH₃)₂ | |
| CO₂CH₃ | CH₃ | CH₃ | OCH₃ | CH(OCH₃)₂ | |
| CO₂CH₃ | CH₃ | CH₃ | CH₃ | CH(OCH₂CH₂O) | |
| CO₂CH₃ | CH₃ | CH₃ | OCH₃ | CH(OCH₂CH₂O) | |
| CO₂CH₃ | CH₃ | CH₃ | CF₃ | CH₃ | |
| CO₂CH₃ | CH₃ | CH₃ | CF₃ | OCH₃ | |
| CO₂CH₃ | CH₃ | CH₃ | OC₂H₅ | CH₃ | |
| CO₂CH₃ | CH₃ | CH₃ | OC₂H₅ | OCH₃ | |
| CO₂CH₃ | CH₃ | CH₃ | CH₃ | OCH₂CF₃ | |
| CO₂CH₃ | CH₃ | CH₃ | OCH₃ | OCH₂CF₃ | |

TABLE VI

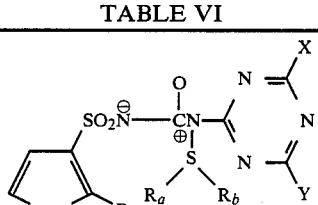

| $R_9$ | $R_a$ | $R_b$ | X | Y | m.p. (°C.) |
|---|---|---|---|---|---|
| F | CH₃ | CH₃ | CH₃ | CH₃ | |
| CH₃ | CH₃ | CH₃ | CH₃ | CH₃ | |
| Cl | CH₃ | CH₃ | CH₃ | CH₃ | |

TABLE VI-continued

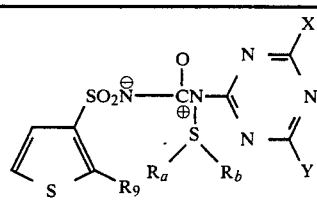

| $R_9$ | $R_a$ | $R_b$ | X | Y | m.p. (°C.) |
|---|---|---|---|---|---|
| Br | CH₃ | CH₃ | CH₃ | CH₃ | |
| NO₂ | CH₃ | CH₃ | CH₃ | CH₃ | |
| SO₂CH₃ | CH₃ | CH₃ | CH₃ | CH₃ | |
| SO₂N(CH₃)₂ | CH₃ | CH₃ | CH₃ | CH₃ | |
| CO₂CH₃ | CH₃ | CH₃ | CH₃ | CH₃ | 110–115° (d) |
| F | CH₃ | CH₃ | CH₃ | OCH₃ | |
| CH₃ | CH₃ | CH₃ | CH₃ | OCH₃ | |
| Cl | CH₃ | CH₃ | CH₃ | OCH₃ | |
| Br | CH₃ | CH₃ | CH₃ | OCH₃ | |
| NO₂ | CH₃ | CH₃ | CH₃ | OCH₃ | |
| SO₂CH₃ | CH₃ | CH₃ | CH₃ | OCH₃ | |
| SO₂N(CH₃)₂ | CH₃ | CH₃ | CH₃ | OCH₃ | |
| CO₂CH₃ | CH₃ | CH₃ | CH₃ | OCH₃ | 98–100° C. |
| CO₂CH₃ | C₂H₅ | C₂H₅ | OCH₃ | OCH₃ | |
| CO₂CH₃ | C₂H₅ | CH₃ | CH₃ | CH₃ | |
| Cl | C₂H₅ | CH₃ | OCH₃ | OCH₃ | |
| Br | C₂H₅ | C₂H₅ | OCH₃ | OCH₃ | |
| NO₂ | C₂H₅ | C₂H₅ | CH₃ | OCH₃ | |
| SO₂CH₃ | C₂H₅ | C₂H₅ | CH₃ | CH₃ | |
| SO₂N(CH₃)₂ | C₂H₅ | C₂H₅ | CH₃ | CH₃ | |
| CO₂CH₃ | C₂H₅ | C₂H₅ | CH₃ | CH₃ | |
| F | CH₃ | CH₃ | OCH₃ | OCH₃ | |
| CH₃ | CH₃ | CH₃ | OCH₃ | OCH₃ | |
| Cl | CH₃ | CH₃ | OCH₃ | OCH₃ | |
| Br | CH₃ | CH₃ | OCH₃ | OCH₃ | |
| NO₂ | CH₃ | CH₃ | OCH₃ | OCH₃ | |
| SO₂CH₃ | CH₃ | CH₃ | OCH₃ | OCH₃ | |
| SO₂N(CH₃)₂ | CH₃ | CH₃ | OCH₃ | OCH₃ | |
| CO₂CH₃ | CH₃ | CH₃ | OCH₃ | OCH₃ | |
| CO₂CH₃ | CH₃ | CH₃ | CH₂F | CH₃ | |
| CO₂CH₃ | CH₃ | CH₃ | OCH₂F | OCH₃ | |
| CO₂CH₃ | CH₃ | CH₃ | CH₃ | C₂H₅ | |
| CO₂CH₃ | CH₃ | CH₃ | OCH₃ | C₂H₅ | |
| CO₂CH₃ | CH₃ | CH₃ | CH₃ | CH₂OCH₃ | |
| CO₂CH₃ | CH₃ | CH₃ | OCH₃ | CH₂OCH₃ | |
| CO₂CH₃ | CH₃ | CH₃ | CH₃ | CH(OCH₃)₂ | |
| CO₂CH₃ | CH₃ | CH₃ | OCH₃ | CH(OCH₃)₂ | |
| CO₂CH₃ | CH₃ | CH₃ | CH₃ | CH(OCH₂CH₂O) | |
| CO₂CH₃ | CH₃ | CH₃ | OCH₃ | CH(OCH₂CH₂O) | |
| CO₂CH₃ | CH₃ | CH₃ | CF₃ | CH₃ | |
| CO₂CH₃ | CH₃ | CH₃ | CF₃ | OCH₃ | |
| CO₂CH₃ | CH₃ | CH₃ | OC₂H₅ | N(CH₃)₂ | |
| CO₂CH₃ | CH₃ | CH₃ | OC₂H₅ | SCH₃ | |
| CO₂CH₃ | CH₃ | CH₃ | CH₃ | OCH₂CF₃ | |
| CO₂CH₃ | CH₃ | CH₃ | OCH₃ | OCH₂CF₃ | |

TABLE VII

| $R_9$ | $R_a$ | $R_b$ | X | Y | m.p.(°C.) |
|---|---|---|---|---|---|
| F | CH₃ | CH₃ | CH₃ | CH₃ | |
| CH₃ | CH₃ | CH₃ | CH₃ | CH₃ | |
| Cl | CH₃ | CH₃ | CH₃ | CH₃ | |
| Br | CH₃ | CH₃ | CH₃ | CH₃ | |
| NO₂ | CH₃ | CH₃ | CH₃ | CH₃ | |
| SO₂CH₃ | CH₃ | CH₃ | CH₃ | CH₃ | |
| SO₂N(CH₃)₂ | CH₃ | CH₃ | CH₃ | CH₃ | |

TABLE VII-continued

| R9 | Ra | Rb | X | Y | m.p.(°C.) |
|---|---|---|---|---|---|
| CO2CH3 | CH3 | CH3 | CH3 | CH3 | |
| F | CH3 | CH3 | CH3 | OCH3 | |
| CH3 | CH3 | CH3 | CH3 | OCH3 | |
| Cl | CH3 | CH3 | CH3 | OCH3 | |
| Br | CH3 | CH3 | CH3 | OCH3 | |
| NO2 | CH3 | CH3 | CH3 | OCH3 | |
| SO2CH3 | CH3 | CH3 | CH3 | OCH3 | |
| SO2N(CH3)2 | CH3 | CH3 | CH3 | OCH3 | |
| CO2CH3 | CH3 | CH3 | CH3 | OCH3 | |
| CO2CH3 | C2H5 | C2H5 | OCH3 | OCH3 | |
| CO2CH3 | C2H5 | CH3 | CH3 | CH3 | |
| Cl | C2H5 | CH3 | OCH3 | OCH3 | |
| Br | C2H5 | C2H5 | OCH3 | OCH3 | |
| NO2 | C2H5 | C2H5 | CH3 | OCH3 | |
| SO2CH3 | C2H5 | C2H5 | CH3 | CH3 | |
| SO2N(CH3)2 | C2H5 | C2H5 | CH3 | CH3 | |
| CO2CH3 | C2H5 | C2H5 | CH3 | CH3 | |
| F | CH3 | CH3 | OCH3 | OCH3 | |
| CH3 | CH3 | CH3 | OCH3 | OCH3 | |
| Cl | CH3 | CH3 | OCH3 | OCH3 | |
| Br | CH3 | CH3 | OCH3 | OCH3 | |
| NO2 | CH3 | CH3 | OCH3 | OCH3 | |
| SO2CH3 | CH3 | CH3 | OCH3 | OCH3 | |
| SO2N(CH3)2 | CH3 | CH3 | OCH3 | OCH3 | |
| CO2CH3 | CH3 | CH3 | OCH3 | OCH3 | |
| CO2CH3 | CH3 | CH3 | Cl | OCH3 | |
| CO2CH3 | CH3 | CH3 | Cl | OC2H5 | |
| CO2CH3 | CH3 | CH3 | Br | CH3 | |
| CO2CH3 | CH3 | CH3 | F | OCH3 | |
| CO2CH3 | CH3 | CH3 | CH3 | C2H5 | |
| CO2CH3 | CH3 | CH3 | OCH3 | C2H5 | |
| CO2CH3 | CH3 | CH3 | CH3 | CH2OCH3 | |
| CO2CH3 | CH3 | CH3 | OCH3 | CH2OCH3 | |
| CO2CH3 | CH3 | CH3 | OCH3 | CH(OCH3)2 | |
| CO2CH3 | CH3 | CH3 | CH3 | CH(OCH2CH2O) | |
| CO2CH3 | CH3 | CH3 | OCH3 | CH(OCH2CH2O) | |
| CO2CH3 | CH3 | CH3 | CF3 | CH3 | |
| CO2CH3 | CH3 | CH3 | CF3 | OCH3 | |
| CO2CH3 | CH3 | CH3 | OC2H5 | N(CH3)2 | |
| CO2CH3 | CH3 | CH3 | OC2H5 | CH2SCH3 | |
| CO2CH3 | CH3 | CH3 | CH3 | OCH2CF3 | |
| CO2CH3 | CH3 | CH3 | OCH3 | OCH2CF3 | |

TABLE VIII

| R9 | Ra | Rb | X | Y | m.p. (°C.) |
|---|---|---|---|---|---|
| F | CH3 | CH3 | CH3 | CH3 | |
| CH3 | CH3 | CH3 | CH3 | CH3 | |
| Cl | CH3 | CH3 | CH3 | CH3 | |
| Br | CH3 | CH3 | CH3 | CH3 | |
| NO2 | CH3 | CH3 | CH3 | CH3 | |
| SO2CH3 | CH3 | CH3 | CH3 | CH3 | |
| SO2N(CH3)2 | CH3 | CH3 | CH3 | CH3 | |
| CO2CH3 | CH3 | CH3 | CH3 | CH3 | |
| F | CH3 | CH3 | CH3 | OCH3 | |
| CH3 | CH3 | CH3 | CH3 | OCH3 | |
| Cl | CH3 | CH3 | CH3 | OCH3 | |
| Br | CH3 | CH3 | CH3 | OCH3 | |
| NO2 | CH3 | CH3 | CH3 | OCH3 | |

TABLE VIII-continued

| R9 | Ra | Rb | X | Y | m.p. (°C.) |
|---|---|---|---|---|---|
| SO2CH3 | CH3 | CH3 | CH3 | OCH3 | |
| SO2N(CH3)2 | CH3 | CH3 | CH3 | OCH3 | |
| CO2CH3 | CH3 | CH3 | CH3 | OCH3 | |
| CO2CH3 | C2H5 | C2H5 | OCH3 | OCH3 | |
| CO2CH3 | C2H5 | CH3 | CH3 | CH3 | |
| Cl | C2H5 | CH3 | OCH3 | OCH3 | |
| Br | C2H5 | C2H5 | OCH3 | OCH3 | |
| NO2 | C2H5 | C2H5 | CH3 | OCH3 | |
| SO2CH3 | C2H5 | C2H5 | CH3 | CH3 | |
| SO2N(CH3)2 | C2H5 | C2H5 | CH3 | CH3 | |
| CO2CH3 | C2H5 | C2H5 | CH3 | CH3 | |
| F | CH3 | CH3 | OCH3 | OCH3 | |
| CH3 | CH3 | CH3 | OCH3 | OCH3 | |
| Cl | CH3 | CH3 | OCH3 | OCH3 | |
| Br | CH3 | CH3 | OCH3 | OCH3 | |
| NO2 | CH3 | CH3 | OCH3 | OCH3 | |
| SO2CH3 | CH3 | CH3 | OCH3 | OCH3 | |
| SO2N(CH3)2 | CH3 | CH3 | OCH3 | OCH3 | |
| CO2CH3 | CH3 | CH3 | OCH3 | OCH3 | |
| CO2CH3 | CH3 | CH3 | CH2F | CH3 | |
| CO2CH3 | CH3 | CH3 | OCF2H | OCH3 | |
| CO2CH3 | CH3 | CH3 | CH3 | C2H5 | |
| CO2CH3 | CH3 | CH3 | OCH3 | C2H5 | |
| CO2CH3 | CH3 | CH3 | CH3 | CH2OCH3 | |
| CO2CH3 | CH3 | CH3 | OCH3 | CH2OCH3 | |
| CO2CH3 | CH3 | CH3 | CH3 | CH(OCH3)2 | |
| CO2CH3 | CH3 | CH3 | OCH3 | CH(OCH3)2 | |
| CO2CH3 | CH3 | CH3 | CH3 | CH(OCH2CH2O) | |
| CO2CH3 | CH3 | CH3 | OCH3 | CH(OCH2CH2O) | |
| CO2CH3 | CH3 | CH3 | CF3 | CH3 | |
| CO2CH3 | CH3 | CH3 | CF3 | OCH3 | |
| CO2CH3 | CH3 | CH3 | OC2H5 | CH3 | |
| CO2CH3 | CH3 | CH3 | OC2H5 | OCH3 | |
| CO2CH3 | CH3 | CH3 | CH3 | OCH2CF3 | |
| CO2CH3 | CH3 | CH3 | OCH3 | OCH2CF3 | |

TABLE IX

| R8 | Ra | Rb | X | Y | m.p. (°C.) |
|---|---|---|---|---|---|
| F | CH3 | CH3 | CH3 | CH3 | |
| CH3 | CH3 | CH3 | CH3 | CH3 | |
| OCH3 | CH3 | CH3 | CH3 | CH3 | |
| Cl | CH3 | CH3 | CH3 | CH3 | |
| SO2CH3 | CH3 | CH3 | CH3 | CH3 | |
| SO2N(CH3)2 | CH3 | CH3 | CH3 | CH3 | |
| Br | CH3 | CH3 | CH3 | OCH3 | |
| CH3 | CH3 | CH3 | CH3 | OCH3 | |
| OCH3 | CH3 | CH3 | CH3 | OCH3 | |
| Cl | CH3 | CH3 | CH3 | OCH3 | |
| SO2CH3 | CH3 | CH3 | CH3 | OCH3 | |
| SO2N(CH3)2 | CH3 | CH3 | CH3 | OCH3 | |
| SO2CH3 | C2H5 | C2H5 | CH3 | CH3 | |
| CH3 | C2H5 | CH3 | CH3 | CH3 | |
| OCH3 | C2H5 | C2H5 | OCH3 | OCH3 | |
| Cl | C2H5 | C2H5 | OCH3 | OCH3 | |
| SO2CH3 | C2H5 | CH3 | CH3 | CH3 | |
| SO2N(CH3)2 | C2H5 | C2H5 | CH3 | CH3 | |
| F | CH3 | CH3 | OCH3 | OCH3 | |
| CH3 | CH3 | CH3 | OCH3 | OCH3 | |
| OCH3 | CH3 | CH3 | OCH3 | OCH3 | |

TABLE IX-continued

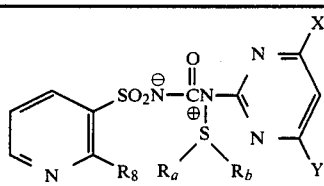

| R8 | Ra | Rb | X | Y | m.p. (°C.) |
|---|---|---|---|---|---|
| Cl | CH3 | CH3 | OCH3 | OCH3 | |
| SO2CH3 | CH3 | CH3 | OCH3 | OCH3 | |
| SO2N(CH3)2 | CH3 | CH3 | OCH3 | OCH3 | |
| SO2CH3 | CH3 | CH3 | Cl | OCH3 | |
| SO2CH3 | CH3 | CH3 | Cl | OC2H5 | |
| SO2CH3 | CH3 | CH3 | F | OCH3 | |
| SO2CH3 | CH3 | CH3 | Br | OCH3 | |
| SO2CH3 | CH3 | CH3 | CH3 | C2H5 | |
| SO2CH3 | CH3 | CH3 | OCH3 | C2H5 | |
| SO2CH3 | CH3 | CH3 | CH3 | CH2OCH3 | |
| SO2CH3 | CH3 | CH3 | OCH3 | CH2OCH3 | |
| SO2CH3 | CH3 | CH3 | CH3 | CH(OCH3)2 | |
| SO2CH3 | CH3 | CH3 | OCH3 | CH(OCH3)2 | |
| SO2CH3 | CH3 | CH3 | CH3 | CH(OCH2CH2O) | |
| SO2CH3 | CH3 | CH3 | OCH3 | CH(OCH2CH2O) | |
| SO2CH3 | CH3 | CH3 | CF3 | CH3 | |
| SO2CH3 | CH3 | CH3 | CF3 | OCH3 | |
| SO2CH3 | CH3 | CH3 | OC2H5 | CH3 | |
| SO2CH3 | CH3 | CH3 | OC2H5 | OCH3 | |
| SO2CH3 | CH3 | CH3 | CH3 | OCH2CF3 | |
| SO2CH3 | CH3 | CH3 | OCH3 | OCH2CF3 | |

TABLE X

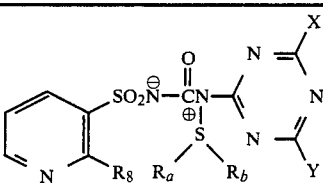

| R8 | Ra | Rb | X | Y | m.p. (°C.) |
|---|---|---|---|---|---|
| F | CH3 | CH3 | CH3 | CH3 | |
| CH3 | CH3 | CH3 | CH3 | CH3 | |

TABLE X-continued

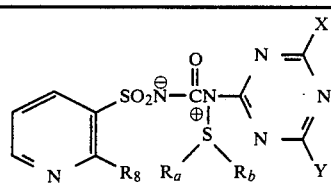

| R8 | Ra | Rb | X | Y | m.p. (°C.) |
|---|---|---|---|---|---|
| OCH3 | CH3 | CH3 | CH3 | CH3 | |
| Cl | CH3 | CH3 | CH3 | CH3 | |
| SO2CH3 | CH3 | CH3 | CH3 | CH3 | |
| SO2N(CH3)2 | CH3 | CH3 | CH3 | CH3 | |
| Br | CH3 | CH3 | CH3 | OCH3 | |
| CH3 | CH3 | CH3 | CH3 | OCH3 | |
| OCH3 | CH3 | CH3 | CH3 | OCH3 | |
| Cl | CH3 | CH3 | CH3 | OCH3 | |
| SO2CH3 | CH3 | CH3 | CH3 | OCH3 | |
| SO2N(CH3)2 | CH3 | CH3 | CH3 | OCH3 | |
| SO2CH3 | C2H5 | C2H5 | CH3 | CH3 | |
| CH3 | C2H5 | CH3 | CH3 | CH3 | |
| OCH3 | C2H5 | CH3 | OCH3 | OCH3 | |
| Cl | C2H5 | C2H5 | OCH3 | OCH3 | |
| SO2CH3 | C2H5 | CH3 | CH3 | CH3 | |
| SO2N(CH3)2 | C2H5 | C2H5 | CH3 | CH3 | |
| F | CH3 | CH3 | OCH3 | OCH3 | |
| CH3 | CH3 | CH3 | OCH3 | OCH3 | |
| OCH3 | CH3 | CH3 | OCH3 | OCH3 | |
| Cl | CH3 | CH3 | OCH3 | OCH3 | |
| SO2CH3 | CH3 | CH3 | OCH3 | OCH3 | |
| SO2N(CH3)2 | CH3 | CH3 | OCH3 | OCH3 | |
| SO2CH3 | CH3 | CH3 | OCF2H | CH3 | |
| SO2CH3 | CH3 | CH3 | OCH2F | OCH3 | |
| SO2CH3 | CH3 | CH3 | CH3 | C2H5 | |
| SO2CH3 | CH3 | CH3 | OCH3 | C2H5 | |
| SO2CH3 | CH3 | CH3 | CH3 | CH2OCH3 | |
| SO2CH3 | CH3 | CH3 | OCH3 | CH2OCH3 | |
| SO2CH3 | CH3 | CH3 | CH3 | CH(OCH3)2 | |
| SO2CH3 | CH3 | CH3 | OCH3 | CH(OCH3)2 | |
| SO2CH3 | CH3 | CH3 | CH3 | CH(OCH2CH2O) | |
| SO2CH3 | CH3 | CH3 | OCH3 | CH(OCH2CH2O) | |
| SO2CH3 | CH3 | CH3 | CF3 | CH3 | |
| SO2CH3 | CH3 | CH3 | CF3 | OCH3 | |
| SO2CH3 | CH3 | CH3 | OC2H5 | CH3 | |
| SO2CH3 | CH3 | CH3 | OC2H5 | OCH3 | |
| SO2CH3 | CH3 | CH3 | CH3 | OCH2CF3 | |
| SO2CH3 | CH3 | CH3 | OCH3 | OCH2CF3 | |

TABLE XI

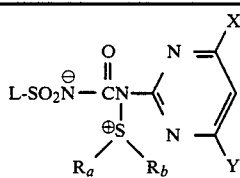

| L | | Ra | Rb | X | Y | m.p. (°C.) |
|---|---|---|---|---|---|---|
| L-6: | R9 = CO2CH3 | CH3 | CH3 | CH3 | CH3 | |
| L-6: | R9 = SO2N(CH3)2 | CH3 | CH3 | CH3 | CH3 | |
| L-6: | R9 = SO2CH3 | CH3 | CH3 | CH3 | CH3 | |
| L-7: | R10 = CO2CH3 | CH3 | CH3 | CH3 | CH3 | |
| L-9: | Q2 = O; R14 = CH3; R15 = H | CH3 | CH3 | CH3 | CH3 | |
| L-9: | Q2 = S; R14 = CH3; R15 = H | CH3 | CH3 | CH3 | CH3 | |
| L-6: | R9 = CO2CH3 | CH3 | CH3 | CH3 | OCH3 | |
| L-6: | R9 = SO2N(CH3)2 | CH3 | CH3 | CH3 | OCH3 | |
| L-6: | R9 = SO2CH3 | CH3 | CH3 | CH3 | OCH3 | |
| L-7: | R10 = CO2CH3 | CH3 | CH3 | CH3 | OCH3 | |
| L-9: | Q2 = O; R14 = CH3; R15 = H | CH3 | CH3 | CH3 | OCH3 | |
| L-9: | Q2 = S; R14 = CH3; R15 = H | CH3 | CH3 | CH3 | OCH3 | |
| L-6: | R9 = CO2CH3 | C2H5 | C2H5 | CH3 | CH3 | |
| L-6: | R9 = SO2N(CH3)2 | C2H5 | CH3 | CH3 | CH3 | |
| L-6: | R9 = SO2CH3 | C2H5 | CH3 | OCH3 | OCH3 | |
| L-6: | R9 = CO2CH3 | C2H5 | C2H5 | OCH3 | OCH3 | |
| L-16: | R17 = H | C2H5 | CH3 | CH3 | CH3 | |
| L-17: | R17 = CH3; R18 = H | C2H5 | C2H5 | CH3 | CH3 | |
| L-6: | R9 = CO2CH3 | CH3 | CH3 | OCH3 | OCH3 | |

TABLE XI-continued

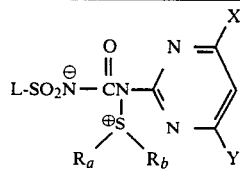

| L | | $R_a$ | $R_b$ | X | Y | m.p. (°C.) |
|---|---|---|---|---|---|---|
| L-6: | $R_9 = SO_2N(CH_3)_2$ | $CH_3$ | $CH_3$ | $OCH_3$ | $OCH_3$ | |
| L-6: | $R_9 = SO_2CH_3$ | $CH_3$ | $CH_3$ | $OCH_3$ | $OCH_3$ | |
| L-7: | $R_{10} = CO_2CH_3$ | $CH_3$ | $CH_3$ | $OCH_3$ | $OCH_3$ | |
| L-9: | $Q_2 = O; R_{14} = CH_3; R_{15} = H$ | $CH_3$ | $CH_3$ | $OCH_3$ | $OCH_3$ | |
| L-9: | $Q_2 = S; R_{14} = CH_3; R_{15} = H$ | $CH_3$ | $CH_3$ | $OCH_3$ | $OCH_3$ | |
| L-8: | $Q_1 = O; R_{11} = R_{12} = CH_3; R_{13} = H; m = 0$ | $CH_3$ | $CH_3$ | $OCH_3$ | $OCH_3$ | |
| L-8: | $Q_1 = S; R_{11} = H; R_{12} = CH_3; R_{13} = H, m = 0$ | $CH_3$ | $C_2H_5$ | $CH_3$ | $OCH_3$ | |
| L-8: | $Q_1 = SO_2; R_{11} = CH_3; R_{12} = H; R_{13} = H; m = 0$ | $CH_3$ | $CH_3$ | $OCH_3$ | $OCH_3$ | |
| L-8: | $Q_1 = SO_2; R_{11} = R_{12} = CH_3; R_{12} = H; m = 1$ | $CH_3$ | $CH_3$ | $CH_3$ | $CH_3$ | |
| L-8: | $Q_1 = SO_2; R_{11} = H; R_{12} = CH_3; R_{13} = H; m = 0$ | $CH_3$ | $CH_3$ | $OCHF_2$ | $OCH_3$ | |
| L-12: | $m = 0; R_{13} = H$ | $CH_3$ | $CH_3$ | $CH_3$ | $CH_3$ | |
| L-13: | $m = 1; R_{13} = H$ | $CH_3$ | $CH_3$ | $CH_3$ | $CH_3$ | |
| L-14: | $R_{16} = CH_3$ | $CH_3$ | $CH_3$ | $CH_3$ | $CH_3$ | |
| L-15: | $R_{17} = H$ | $CH_3$ | $CH_3$ | $CH_3$ | $CH_3$ | |
| L-16: | $R_{17} = H$ | $CH_3$ | $CH_3$ | $CH_3$ | $CH_3$ | |
| L-17: | $R_{17} = CH_3; R_{18} = H$ | $CH_3$ | $CH_3$ | $CH_3$ | $CH_3$ | |
| L-12: | $m = 0; R_{13} = H$ | $CH_3$ | $CH_3$ | $CH_3$ | $OCH_3$ | |
| L-13: | $m = 1; R_{13} = H$ | $CH_3$ | $CH_3$ | $CH_3$ | $OCH_3$ | |
| L-14: | $R_{16} = CH_3$ | $CH_3$ | $CH_3$ | $CH_3$ | $OCH_3$ | |
| L-15: | $R_{17} = H$ | $CH_3$ | $CH_3$ | $CH_3$ | $OCH_3$ | |
| L-16: | $R_{17} = H$ | $CH_3$ | $CH_3$ | $CH_3$ | $OCH_3$ | |
| L-17: | $R_{17} = CH_3; R_{18} = H$ | $CH_3$ | $CH_3$ | $CH_3$ | $OCH_3$ | |
| L-7: | $R_{10} = CO_2CH_3$ | $C_2H_5$ | $C_2H_5$ | $CH_3$ | $CH_3$ | |
| L-9: | $Q_2 = O; R_{14} = CH_3; R_{15} = H$ | $C_2H_5$ | $CH_3$ | $CH_3$ | $CH_3$ | |
| L-12: | $m = 0; R_{13} = H$ | $C_2H_5$ | $CH_3$ | $OCH_3$ | $OCH_3$ | |
| L-13: | $m = 1; R_{13} = H$ | $C_2H_5$ | $C_2H_5$ | $OCH_3$ | $OCH_3$ | |
| L-14: | $R_{16} = CH_3$ | $C_2H_5$ | $C_2H_5$ | $CH_3$ | $CH_3$ | |
| L-15: | $R_{17} = H$ | $C_2H_5$ | $C_2H_5$ | $CH_3$ | $CH_3$ | |
| L-12: | $m = 0; R_{13} = H$ | $CH_3$ | $CH_3$ | $OCH_3$ | $OCH_3$ | |
| L-13: | $m = 1; R_{13} = H$ | $CH_3$ | $CH_3$ | $OCH_3$ | $OCH_3$ | |
| L-14: | $R_{16} = CH_3$ | $CH_3$ | $CH_3$ | $OCH_3$ | $OCH_3$ | |
| L-15: | $R_{17} = H$ | $CH_3$ | $CH_3$ | $OCH_3$ | $OCH_3$ | |
| L-16: | $R_{17} = H$ | $CH_3$ | $CH_3$ | $OCH_3$ | $OCH_3$ | |
| L-17: | $R_{17} = CH_3; R_{18} = CH_3$ | $CH_3$ | $CH_3$ | $OCH_3$ | $OCH_3$ | |
| L-10: | $R_{13} = H; R_{16} = CH_3; m = 0$ | $CH_3$ | $CH_3$ | $OCH_3$ | $OCH_3$ | |
| L-10: | $R_{13} = H; R_{16} = C_2H_5; m = 0$ | $CH_3$ | $C_2H_5$ | $CH_3$ | $OCH_3$ | |
| L-10: | $R_{13} = CH_3; R_{16} = CH_3; m = 0$ | $C_2H_5$ | $C_2H_5$ | $CH_3$ | $CH_3$ | |
| L-11: | $R_{13} = H; m = 0$ | $CH_3$ | $CH_3$ | $OCH_3$ | $OCH_3$ | |
| L-11: | $R_{13} = H; m = 1$ | $CH_3$ | $CH_3$ | $Cl$ | $OCH_3$ | |
| L-11: | $R_{13} = CH_3; m = 0$ | $C_2H_5$ | $CH_3$ | $CH_3$ | $CH(OCH_3)_2$ | |

TABLE XII

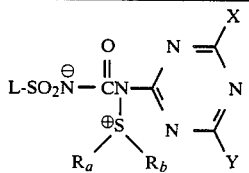

| L | | $R_a$ | $R_b$ | X | Y | m.p. (° C.) |
|---|---|---|---|---|---|---|
| L-6: | $R_9 = CO_2CH_3$ | $CH_3$ | $CH_3$ | $CH_3$ | $CH_3$ | |
| L-6: | $R_9 = SO_2N(CH_3)_2$ | $CH_3$ | $CH_3$ | $CH_3$ | $CH_3$ | |
| L-6: | $R_9 = SO_2CH_3$ | $CH_3$ | $CH_3$ | $CH_3$ | $CH_3$ | |
| L-7: | $R_{10} = CO_2CH_3$ | $CH_3$ | $CH_3$ | $CH_3$ | $CH_3$ | |
| L-9: | $Q_2 = O; R_{14} = CH_3; R_{15} = H$ | $CH_3$ | $CH_3$ | $CH_3$ | $CH_3$ | |
| L-9: | $Q_2 = S; R_{14} = CH_3; R_{15} = H$ | $CH_3$ | $CH_3$ | $CH_3$ | $CH_3$ | |
| L-6: | $R_9 = CO_2CH_3$ | $CH_3$ | $CH_3$ | $CH_3$ | $OCH_3$ | |
| L-6: | $R_9 = SO_2N(CH_3)_2$ | $CH_3$ | $CH_3$ | $CH_3$ | $OCH_3$ | |
| L-6: | $R_9 = SO_2CH_3$ | $CH_3$ | $CH_3$ | $CH_3$ | $OCH_3$ | |
| L-7: | $R_{10} = CO_2CH_3$ | $CH_3$ | $CH_3$ | $CH_3$ | $CH_3$ | |
| L-9: | $Q_2 = O; R_{14} = CH_3; R_{15} = H$ | $CH_3$ | $CH_3$ | $CH_3$ | $OCH_3$ | |
| L-9: | $Q_2 = S; R_{14} = CH_3; R_{15} = H$ | $CH_3$ | $CH_3$ | $CH_3$ | $OCH_3$ | |
| L-6: | $R_9 = CO_2CH_3$ | $C_2H_5$ | $C_2H_5$ | $CH_3$ | $CH_3$ | |
| L-6: | $R_9 = SO_2N(CH_3)_2$ | $C_2H_5$ | $CH_3$ | $CH_3$ | $CH_3$ | |
| L-6: | $R_9 = SO_2CH_3$ | $C_2H_5$ | $CH_3$ | $OCH_3$ | $OCH_3$ | |
| L-6: | $R_9 = CO_2CH_3$ | $C_2H_5$ | $C_2H_5$ | $OCH_3$ | $OCH_3$ | |
| L-16: | $R_{17} = H$ | $C_2H_5$ | $CH_3$ | $CH_3$ | $CH_3$ | |

TABLE XII-continued $$\text{L-SO}_2\overset{\ominus}{\text{N}}-\overset{\overset{O}{\|}}{\underset{\underset{R_a\ R_b}{\overset{\oplus}{S}}}{C}}\text{N}\overset{\displaystyle N=\overset{X}{\underset{Y}{\bigtriangleup}}}{}$$

| L | | $R_a$ | $R_b$ | X | Y | m.p. (° C.) |
|---|---|---|---|---|---|---|
| L-17: | $R_{17}$ = CH$_3$; $R_{18}$ = H | C$_2$H$_5$ | C$_2$H$_5$ | CH$_3$ | CH$_3$ | |
| L-6: | $R_9$ = CO$_2$CH$_3$ | CH$_3$ | CH$_3$ | OCH$_3$ | OCH$_3$ | |
| L-6: | $R_9$ = SO$_2$N(CH$_3$)$_2$ | CH$_3$ | CH$_3$ | OCH$_3$ | OCH$_3$ | |
| L-6: | $R_9$ = SO$_2$CH$_3$ | CH$_3$ | CH$_3$ | OCH$_3$ | OCH$_3$ | |
| L-7: | $R_{10}$ = CO$_2$CH$_3$ | CH$_3$ | CH$_3$ | OCH$_3$ | OCH$_3$ | |
| L-9: | $Q_2$ = O; $R_{14}$ = CH$_3$; $R_{15}$ = H | CH$_3$ | CH$_3$ | OCH$_3$ | OCH$_3$ | |
| L-9: | $Q_2$ = S; $R_{14}$ = CH$_3$; $R_{15}$ = H | CH$_3$ | CH$_3$ | OCH$_3$ | OCH$_3$ | |
| L-8: | $Q_1$ = O; $R_{11}$ = $R_{12}$ = CH$_3$; $R_{13}$ = H; m = 0 | CH$_3$ | CH$_3$ | OCH$_3$ | OCH$_3$ | |
| L-8: | $Q_1$ = S; $R_{11}$ = H; $R_{12}$ = CH$_3$; $R_{13}$ = H, m = 0 | CH$_3$ | C$_2$H$_5$ | CH$_3$ | OCH$_3$ | |
| L-8: | $Q_1$ = SO$_2$; $R_{11}$ = CH$_3$; $R_{12}$ = H; $R_{13}$ = H; m = 0 | CH$_3$ | CH$_3$ | OCH$_3$ | OCH$_3$ | |
| L-8: | $Q_1$ = SO$_2$; $R_{11}$ = $R_{12}$ = CH$_3$; $R_{13}$ = H; m = 1 | CH$_3$ | CH$_3$ | CH$_3$ | CH$_3$ | |
| L-8: | $Q_1$ = SO$_2$; $R_{11}$ = H; $R_{12}$ = CH$_3$, $R_{13}$ = H; m = 0 | CH$_3$ | CH$_3$ | OCHF$_2$ | OCH$_3$ | |
| L-12: | m = 0; $R_{13}$ = H | CH$_3$ | CH$_3$ | CH$_3$ | CH$_3$ | |
| L-13: | m = 1; $R_{13}$ = H | CH$_3$ | CH$_3$ | CH$_3$ | CH$_3$ | |
| L-14: | $R_{16}$ = CH$_3$ | CH$_3$ | CH$_3$ | CH$_3$ | CH$_3$ | |
| L-15: | $R_{17}$ = H | CH$_3$ | CH$_3$ | CH$_3$ | CH$_3$ | |
| L-16: | $R_{17}$ = H | CH$_3$ | CH$_3$ | CH$_3$ | CH$_3$ | |
| L-17: | $R_{17}$ = CH$_3$; $R_{18}$ = H | CH$_3$ | CH$_3$ | CH$_3$ | CH$_3$ | |
| L-12: | m = 0; $R_{13}$ = H | CH$_3$ | CH$_3$ | CH$_3$ | OCH$_3$ | |
| L-13: | m = 1; $R_{13}$ = H | CH$_3$ | CH$_3$ | CH$_3$ | OCH$_3$ | |
| L-14: | $R_{16}$ = CH$_3$ | CH$_3$ | CH$_3$ | CH$_3$ | OCH$_3$ | |
| L-15: | $R_{17}$ = H | CH$_3$ | CH$_3$ | CH$_3$ | OCH$_3$ | |
| L-16: | $R_{17}$ = H | CH$_3$ | CH$_3$ | CH$_3$ | OCH$_3$ | |
| L-17: | $R_{17}$ = CH$_3$; $R_{18}$ = H | CH$_3$ | CH$_3$ | CH$_3$ | OCH$_3$ | |
| L-7: | $R_{10}$ = CO$_2$CH$_3$ | C$_2$H$_5$ | C$_2$H$_5$ | CH$_3$ | CH$_3$ | |
| L-9: | $Q_2$ = O; $R_{14}$ = CH$_3$; $R_{15}$ = H | C$_2$H$_5$ | CH$_3$ | CH$_3$ | CH$_3$ | |
| L-12: | m = ; $R_{13}$ = H | C$_2$H$_5$ | CH$_3$ | OCH$_3$ | OCH$_3$ | |
| L-13: | m = 1; $R_{13}$ = H | C$_2$H$_5$ | C$_2$H$_5$ | OCH$_3$ | OCH$_3$ | |
| L-14: | $R_{16}$ = CH$_3$ | C$_2$H$_5$ | CH$_3$ | CH$_3$ | CH$_3$ | |
| L-15: | $R_{17}$ = H | C$_2$H$_5$ | C$_2$H$_5$ | CH$_3$ | CH$_3$ | |
| L-12: | m = 0; $R_{13}$ = H | CH$_3$ | CH$_3$ | OCH$_3$ | OCH$_3$ | |
| L-13: | m = 1; $R_{13}$ = H | CH$_3$ | CH$_3$ | OCH$_3$ | OCH$_3$ | |
| L-14: | $R_{16}$ = CH$_3$ | CH$_3$ | CH$_3$ | OCH$_3$ | OCH$_3$ | |
| L-15: | $R_{17}$ = H | CH$_3$ | CH$_3$ | OCH$_3$ | OCH$_3$ | |
| L-16: | $R_{17}$ = H | CH$_3$ | CH$_3$ | OCH$_3$ | OCH$_3$ | |
| L-17: | $R_{17}$ = CH$_3$; $R_{18}$ = CH$_3$ | CH$_3$ | CH$_3$ | OCH$_3$ | OCH$_3$ | |
| L-10: | $R_{13}$ = H; $R_{16}$ = CH$_3$; m = 0 | CH$_3$ | CH$_3$ | OCH$_3$ | OCH$_3$ | |
| L-10: | $R_{13}$ = H; $R_{16}$ = C$_2$C$_5$; m = 0 | CH$_3$ | C$_2$H$_5$ | CH$_3$ | OCH$_3$ | |
| L-10: | $R_{13}$ = CH$_3$; $R_{16}$ = CH$_3$; m = 0 | C$_2$H$_5$ | C$_2$H$_5$ | CH$_3$ | CH$_3$ | |
| L-11: | $R_{13}$ = H; m = 0 | CH$_3$ | CH$_3$ | OCH$_3$ | OCHF$_2$ | |
| L-11: | $R_{13}$ = H; m = 1 | CH$_3$ | CH$_3$ | CF$_3$ | OCH$_3$ | |
| L-11: | $R_{13}$ = CH$_3$; m = 0 | C$_2$H$_5$ | CH$_3$ | CH$_3$ | CH(OCH$_3$)$_2$ | |

TABLE XIII $$\text{L-SO}_2\overset{\ominus}{\text{N}}-\overset{\overset{O}{\|}}{\underset{\underset{R_a\ R_b}{\overset{\oplus}{S}}}{C}}\text{N}\overset{\displaystyle\begin{array}{c}CH_3\\N\end{array}}{\underset{\displaystyle\begin{array}{c}N\\O\end{array}}{\bigtriangleup}}$$

| L | | $R_a$ | $R_b$ |
|---|---|---|---|
| L-1: | $R_5$ = CO$_2$CH$_3$; $R_6$ = H | C$_2$H$_5$ | C$_2$H$_5$ |
| L-1: | $R_5$ = CO$_2$CH$_3$; $R_6$ = H | CH$_3$ | C$_2$H$_5$ |
| L-1: | $R_5$ = CO$_2$CH$_3$; $R_6$ = H | CH$_3$ | CH$_3$ |
| L-1: | $R_5$ = CO$_2$CH$_3$; $R_6$ = 5-OCH$_3$ | CH$_3$ | CH$_3$ |
| L-1: | $R_5$ = SO$_2$N(CH$_3$)$_2$; $R_6$ = H | CH$_3$ | CH$_3$ |
| L-1: | $R_5$ = SO$_2$CH$_3$; $R_6$ = H | CH$_3$ | CH$_3$ |
| L-1: | $R_5$ = Cl; $R_6$ = H | CH$_3$ | CH$_3$ |
| L-1: | $R_5$ = SO$_2$CH$_2$CH$_2$CH$_3$; $R_6$ = H | CH$_3$ | CH$_3$ |
| L-2: | $R_7$ = SO$_2$CH$_3$ | CH$_3$ | CH$_3$ |
| L-3: | $R_8$ = SO$_2$N(CH$_3$)$_2$ | CH$_3$ | CH$_3$ |
| L-4: | $R_9$ = CO$_2$CH$_3$ | CH$_3$ | CH$_3$ |
| L-5: | $R_9$ = CO$_2$CH$_3$ | CH$_3$ | CH$_3$ |
| L-6: | $R_9$ = CO$_2$CH$_3$ | CH$_3$ | CH$_3$ |
| L-7: | $R_{10}$ = CO$_2$CH$_3$ | CH$_3$ | CH$_3$ |
| L-8: | $Q_1$ = O; m = 0; $R_{11}$ = CH$_3$; $R_{12}$ = CH$_3$; | CH$_3$ | CH$_3$ |

TABLE XIII-continued $$\text{L-SO}_2\overset{\ominus}{\text{N}}-\overset{\overset{O}{\|}}{\underset{\underset{R_a\ R_b}{\overset{\oplus}{S}}}{C}}\text{N}\overset{\displaystyle\begin{array}{c}CH_3\\N\end{array}}{\underset{\displaystyle\begin{array}{c}N\\O\end{array}}{\bigtriangleup}}$$

| L | | $R_a$ | $R_b$ |
|---|---|---|---|
| | $R_{13}$ = H | | |
| L-9: | Q = O; $R_{14}$ = CH$_3$; $R_{15}$ = H | CH$_3$ | CH$_3$ |
| L-10: | m = 0; $R_{16}$ = CH$_3$; $R_{13}$ = H | CH$_3$ | CH$_3$ |
| L-11: | m = 1; $R_{13}$ = H | CH$_3$ | CH$_3$ |
| L-11: | m = 0; $R_{13}$ = H | CH$_3$ | CH$_3$ |
| L-12: | m = 0; $R_{13}$ = H | CH$_3$ | CH$_3$ |
| L-13: | m = 1; $R_{13}$ = H | CH$_3$ | CH$_3$ |
| L-14: | $R_{16}$ = CH$_3$ | CH$_3$ | CH$_3$ |
| L-15: | $R_{17}$ = H | CH$_3$ | CH$_3$ |
| L-16: | $R_{17}$ = H | CH$_3$ | CH$_3$ |
| L-17: | $R_{17}$ = CH$_3$; $R_{18}$ = H | CH$_3$ | CH$_3$ |

TABLE XIV

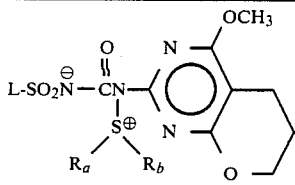

| L | | $R_a$ | $R_b$ |
|---|---|---|---|
| L-1: | $R_5 = CO_2CH_3$; $R_6 = H$ | $C_2H_5$ | $C_2H_5$ |
| L-1: | $R_5 = CO_2CH_3$; $R_6 = H$ | $CH_3$ | $C_2H_5$ |
| L-1: | $R_5 = CO_2CH_3$; $R_6 = H$ | $CH_3$ | $CH_3$ |
| L-1: | $R_5 = CO_2CH_3$; $R_6 = 5\text{-}OCH_3$ | $CH_3$ | $CH_3$ |
| L-1: | $R_5 = SO_2N(CH_3)_2$; $R_6 = H$ | $CH_3$ | $CH_3$ |
| L-1: | $R_5 = SO_2CH_3$; $R_6 = H$ | $CH_3$ | $CH_3$ |
| L-1: | $R_5 = Cl$; $R_6 = H$ | $CH_3$ | $CH_3$ |
| L-1: | $R_5 = SO_2CH_2CH_2CH_3$; $R_6 = H$ | $CH_3$ | $CH_3$ |
| L-2: | $R_7 = SO_2CH_3$ | $CH_3$ | $CH_3$ |
| L-3: | $R_8 = SO_2N(CH_3)_2$ | $CH_3$ | $CH_3$ |
| L-4: | $R_9 = CO_2CH_3$ | $CH_3$ | $CH_3$ |
| L-5: | $R_9 = CO_2CH_3$ | $CH_3$ | $CH_3$ |
| L-6: | $R_9 = CO_2CH_3$ | $CH_3$ | $CH_3$ |
| L-7: | $R_{10} = CO_2CH_3$ | $CH_3$ | $CH_3$ |
| L-8: | $Q_1 = O$; $m = 0$; $R_{11} = CH_3$; $R_{12} = CH_3$; $R_{13} = H$ | $CH_3$ | $CH_3$ |
| L-9: | $Q = O$, $R_{14} = CH_3$; $R_{15} = H$ | $CH_3$ | $CH_3$ |
| L-10: | $m = 0$; $R_{16} = CH_3$; $R_{13} = H$ | $CH_3$ | $CH_3$ |
| L-11: | $m = 1$; $R_{13} = H$ | $CH_3$ | $CH_3$ |
| L-11: | $m = 0$; $R_{13} = H$ | $CH_3$ | $CH_3$ |
| L-12: | $m = 0$; $R_{13} = H$ | $CH_3$ | $CH_3$ |
| L-13: | $m = 1$; $R_{13} = H$ | $CH_3$ | $CH_3$ |
| L-14: | $R_{16} = CH_3$ | $CH_3$ | $CH_3$ |
| L-15: | $R_{17} = H$ | $CH_3$ | $CH_3$ |
| L-16: | $R_{17} = H$ | $CH_3$ | $CH_3$ |
| L-17: | $R_{17} = CH_3$; $R_{18} = H$ | $CH_3$ | $CH_3$ |

TABLE XVI

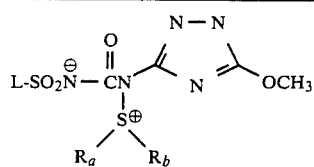

| L | | $R_a$ | $R_b$ |
|---|---|---|---|
| L-1: | $R_5 = CO_2CH_3$; $R_6 = H$ | $C_2H_5$ | $C_2H_5$ |
| L-1: | $R_5 = CO_2CH_3$; $R_6 = H$ | $CH_3$ | $C_2H_5$ |
| L-1: | $R_5 = CO_2CH_3$; $R_6 = H$ | $CH_3$ | $CH_3$ |
| L-1: | $R_5 = CO_2CH_3$; $R_6 = 5\text{-}OCH_3$ | $CH_3$ | $CH_3$ |
| L-1: | $R_5 = SO_2N(CH_3)_2$; $R_6 = H$ | $CH_3$ | $CH_3$ |
| L-1: | $R_5 = SO_2CH_3$; $R_6 = H$ | $CH_3$ | $CH_3$ |
| L-1: | $R_5 = Cl$; $R_6 = H$ | $CH_3$ | $CH_3$ |
| L-1: | $R_5 = SO_2CH_2CH_2CH_3$; $R_6 = H$ | $CH_3$ | $CH_3$ |
| L-2: | $R_7 = SO_2CH_3$ | $CH_3$ | $CH_3$ |
| L-3: | $R_8 = SO_2N(CH_3)_2$ | $CH_3$ | $CH_3$ |
| L-4: | $R_9 = CO_2CH_3$ | $CH_3$ | $CH_3$ |
| L-5: | $R_9 = CO_2CH_3$ | $CH_3$ | $CH_3$ |
| L-6: | $R_9 = CO_2CH_3$ | $CH_3$ | $CH_3$ |
| L-7: | $R_{10} = CO_2CH_3$ | $CH_3$ | $CH_3$ |
| L-8: | $Q_1 = O$; $m = 0$; $R_{11} = CH_3$; $R_{12} = CH_3$; $R_{13} = H$ | $CH_3$ | $CH_3$ |
| L-9: | $Q = O$, $R_{14} = CH_3$; $R_{15} = H$ | $CH_3$ | $CH_3$ |
| L-10: | $m = 0$; $R_{16} = CH_3$; $R_{13} = H$ | $CH_3$ | $CH_3$ |
| L-11: | $m = 1$; $R_{13} = H$ | $CH_3$ | $CH_3$ |
| L-11: | $m = 0$; $R_{13} = H$ | $CH_3$ | $CH_3$ |
| L-12: | $m = 0$; $R_{13} = H$ | $CH_3$ | $CH_3$ |
| L-13: | $m = 1$; $R_{13} = H$ | $CH_3$ | $CH_3$ |
| L-14: | $R_{16} = CH_3$ | $CH_3$ | $CH_3$ |
| L-15: | $R_{17} = H$ | $CH_3$ | $CH_3$ |
| L-16: | $R_{17} = H$ | $CH_3$ | $CH_3$ |
| L-17: | $R_{17} = CH_3$; $R_{18} = H$ | $CH_3$ | $CH_3$ |

TABLE XV

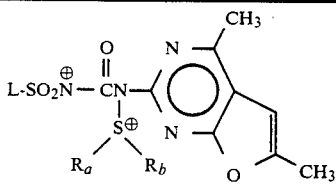

| L | | $R_a$ | $R_b$ |
|---|---|---|---|
| L-1: | $R_5 = CO_2CH_3$; $R_6 = H$ | $C_2H_5$ | $C_2H_5$ |
| L-1: | $R_5 = CO_2CH_3$; $R_6 = H$ | $CH_3$ | $C_2H_5$ |
| L-1: | $R_5 = CO_2CH_3$; $R_6 = H$ | $CH_3$ | $CH_3$ |
| L-1: | $R_5 = CO_2CH_3$; $R_6 = 5\text{-}OCH_3$ | $CH_3$ | $CH_3$ |
| L-1: | $R_5 = SO_2N(CH_3)_2$; $R_6 = H$ | $CH_3$ | $CH_3$ |
| L-1: | $R_5 = SO_2CH_3$; $R_6 = H$ | $CH_3$ | $CH_3$ |
| L-1: | $R_5 = Cl$; $R_6 = H$ | $CH_3$ | $CH_3$ |
| L-1: | $R_5 = SO_2CH_2CH_2CH_3$; $R_6 = H$ | $CH_3$ | $CH_3$ |
| L-2: | $R_7 = SO_2CH_3$ | $CH_3$ | $CH_3$ |
| L-3: | $R_8 = SO_2N(CH_3)_2$ | $CH_3$ | $CH_3$ |
| L-4: | $R_9 = CO_2CH_3$ | $CH_3$ | $CH_3$ |
| L-5: | $R_9 = CO_2CH_3$ | $CH_3$ | $CH_3$ |
| L-6: | $R_9 = CO_2CH_3$ | $CH_3$ | $CH_3$ |
| L-7: | $R_{10} = CO_2CH_3$ | $CH_3$ | $CH_3$ |
| L-8: | $Q_1 = O$; $m = 0$; $R_{11} = CH_3$; $R_{12} = CH_3$; $R_{13} = H$ | $CH_3$ | $CH_3$ |
| L-9: | $Q = O$, $R_{14} = CH_3$; $R_{15} = H$ | $CH_3$ | $CH_3$ |
| L-10: | $m = 0$; $R_{16} = CH_3$; $R_{13} = H$ | $CH_3$ | $CH_3$ |
| L-11: | $m = 1$; $R_{13} = H$ | $CH_3$ | $CH_3$ |
| L-11: | $m = 0$; $R_{13} = H$ | $CH_3$ | $CH_3$ |
| L-12: | $m = 0$; $R_{13} = H$ | $CH_3$ | $CH_3$ |
| L-13: | $m = 1$; $R_{13} = H$ | $CH_3$ | $CH_3$ |
| L-14: | $R_{16} = CH_3$ | $CH_3$ | $CH_3$ |
| L-15: | $R_{17} = H$ | $CH_3$ | $CH_3$ |
| L-16: | $R_{17} = H$ | $CH_3$ | $CH_3$ |
| L-17: | $R_{17} = CH_3$; $R_{18} = H$ | $CH_3$ | $CH_3$ |

TABLE XVII

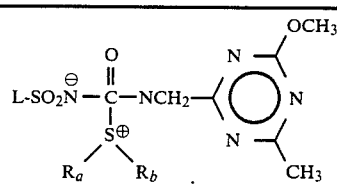

| L | | $R_a$ | $R_b$ |
|---|---|---|---|
| L-1: | $R_5 = CO_2CH_3$; $R_6 = H$ | $C_2H_5$ | $C_2H_5$ |
| L-1: | $R_5 = CO_2CH_3$; $R_6 = H$ | $CH_3$ | $C_2H_5$ |
| L-1: | $R_5 = CO_2CH_3$; $R_6 = H$ | $CH_3$ | $CH_3$ |
| L-1: | $R_5 = CO_2CH_3$; $R_6 = 5\text{-}OCH_3$ | $CH_3$ | $CH_3$ |
| L-1: | $R_5 = SO_2N(CH_3)_2$; $R_6 = H$ | $CH_3$ | $CH_3$ |
| L-1: | $R_5 = SO_2CH_3$; $R_6 = H$ | $CH_3$ | $CH_3$ |
| L-1: | $R_5 = Cl$; $R_6 = H$ | $CH_3$ | $CH_3$ |
| L-1: | $R_5 = SO_2CH_2CH_2CH_3$; $R_6 = H$ | $CH_3$ | $CH_3$ |
| L-2: | $R_7 = SO_2CH_3$ | $CH_3$ | $CH_3$ |
| L-3: | $R_8 = SO_2N(CH_3)_2$ | $CH_3$ | $CH_3$ |
| L-4: | $R_9 = CO_2CH_3$ | $CH_3$ | $CH_3$ |
| L-5: | $R_9 = CO_2CH_3$ | $CH_3$ | $CH_3$ |
| L-6: | $R_9 = CO_2CH_3$ | $CH_3$ | $CH_3$ |
| L-7: | $R_{10} = CO_2CH_3$ | $CH_3$ | $CH_3$ |
| L-8: | $Q_1 = O$; $m = 0$; $R_{11} = CH_3$; $R_{12} = CH_3$; $R_{13} = H$ | $CH_3$ | $CH_3$ |
| L-9: | $Q_2 = O$, $R_{14} = CH_3$; $R_{15} = H$ | $CH_3$ | $CH_3$ |
| L-10: | $m = 0$; $R_{16} = CH_3$; $R_{13} = H$ | $CH_3$ | $CH_3$ |
| L-11: | $m = 1$; $R_{13} = H$ | $CH_3$ | $CH_3$ |
| L-11: | $m = 0$; $R_{13} = H$ | $CH_3$ | $CH_3$ |
| L-12: | $m = 0$; $R_{13} = H$ | $CH_3$ | $CH_3$ |
| L-13: | $m = 1$; $R_{13} = H$ | $CH_3$ | $CH_3$ |
| L-14: | $R_{16} = CH_3$ | $CH_3$ | $CH_3$ |
| L-15: | $R_{17} = H$ | $CH_3$ | $CH_3$ |
| L-16: | $R_{17} = H$ | $CH_3$ | $CH_3$ |
| L-17: | $R_{17} = CH_3$; $R_{18} = H$ | $CH_3$ | $CH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XVIII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

Wettable Powder

N-[(4,6-dimethoxypyrimidin-2-yl)aminocarbonyl]-2-dimethylaminosulfonylbenzenesulfonamide,
 dimethylsulfonium inner salt: 80%
sodium alkylnaphthalenesulfone: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 5

Wettable Powder

N-[(4,6-dimethoxypyrimidin-2-yl)aminocarbonyl]-2-dimethylaminosulfonylbenzenesulfonamide,
 dimethylsulfonium inner salt: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 6

Granule

Wettable Powder of Example 5: 5%
attapulgite granules: 95%
(U.S.S. 20–40 mesh; 0.84–0.42 mm)

A slurry of wettable powder containing ≈25% solids is sprayed on the surface of attapulgite granules in a double-cone blender. The granules are dried and packaged.

EXAMPLE 7

Extruded Pellet

2-[[(4,6-dimethoxypyrimidin-2-yl)aminocarbonyl]-2-dimethylaminosulfonyl]benzoic acid methyl ester,
 dimethylsulfonium inner salt: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Oil Suspension

N-[(4,6-dimethoxypyrimidin-2-yl)aminocarbonyl]-2-dimethylaminosulfonylbenzenensulfonamide,
    dimethylsulfonium inner salt: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 9

Wettable Powder

2-[[(4,6-dimethoxypyrimidin-2-yl)aminocarbonyl]-2-dimethylaminosulfonyl]benzoic acid methyl ester,
    dimethylsulfonium inner salt: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

Low Strength Granule

N-[(4,6-dimethylpyrimidin-2-yl)aminocarbonyl]-2-dimethylaminosulfonylbenzenesulfonamide,
    dimethylsulfonium inner salt: 1%
N,N-dimethylformamide: 9%
attapulgite granules: 90%
(U.S.S. 20–40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 11

Aqueous Suspension

N-[(4,6-dimethoxypyrimidin-2-yl)aminocarbonyl]-2-dimethylaminosulfonylbenzenesulfonamide,
    dimethylsulfonium inner salt: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 12

Low Strength Granule

2-[[(4-methoxy-6-methylpyrimidin-2-yl)aminocarbonyl]aminosulfonyl]benzoic acid methyl ester,
    dimethylsulfonium inner salt: 0.1%
attapulgite granules: 99.9%
(U.S.S. 20–40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

N-[(4,6-dimethoxypyrimidin-2-yl)aminocarbonyl]-2-dimethylaminosulfonylbenzenesulfonamide,
    dimethylsulfonium inner salt: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 14

High Strength Concentrate

N-[(4,6-dimethoxypyrimidin-2-yl)aminocarbonyl]-2-dimethylaminosulfonylbenzenesulfonamide,
    dimethylsulfonium inner salt: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

N-[(4,6-dimethoxypyrimidin-2-yl)aminocarbonyl]-2-dimethylaminosulfonylbenzenesulfonamide,
    dimethylsulfonium inner salt: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 16

Wettable Powder

N-[(4,6-dimethoxypyrimidin-2-yl)aminocarbonyl]-2-dimethylaminosulfonylbenzenesulfonamide,
    dimethylsulfonium inner salt: 40% sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 17

Oil Suspension

N-[(4,6-dimethoxypyrimidin-2-yl)aminocarbonyl]-2-dimethylaminosulfonylbenzenesulfonamide,
  dimethylsulfonium inner salt: 35%
blend of polyalcohol carboxylic esters and oil soluble
  petroleum sulfonates: 6%
xylene: 59%

The ingredients are combined and ground together in a sand mill to produce particles essentially all below 5 microns. The product can be used directly, extended with oils, or emulsified in water.

EXAMPLE 18

Dust

2-[[(4,6-dimethoxypyrimidin-2-yl)aminocarbonyl]-aminosulfonyl]benzoic acid methyl ester,
  dimethylsulfonium inner salt: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds should be useful for the selective pre- or post-emergence weed control in crops, such as wheat and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with one another or with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (*Digitaria* sp.), barnyard-grass (*Echinochloa crusgalli*), wild oats (*Avena fatua*), sicklepod (*Cassia obtusifolia*), morningglory (*Ipomoea* sp.), cocklebur (*Xanthium* sp.), sorghum, corn, soybean, rice, wheat and nutsedge (*Cyperus rotundus*) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effect;
U=unusual pigmentation; and
6Y=abscised buds or flowers.

The compounds tested are highly active herbicides. Several of the compounds in Table A selectively control weeds applied pre- or post-emergence to wheat.

Compounds

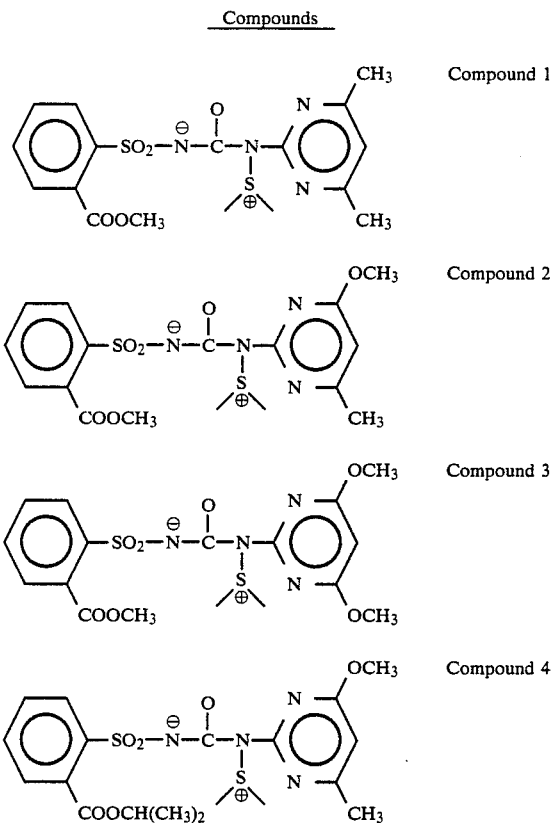

-continued
Compounds

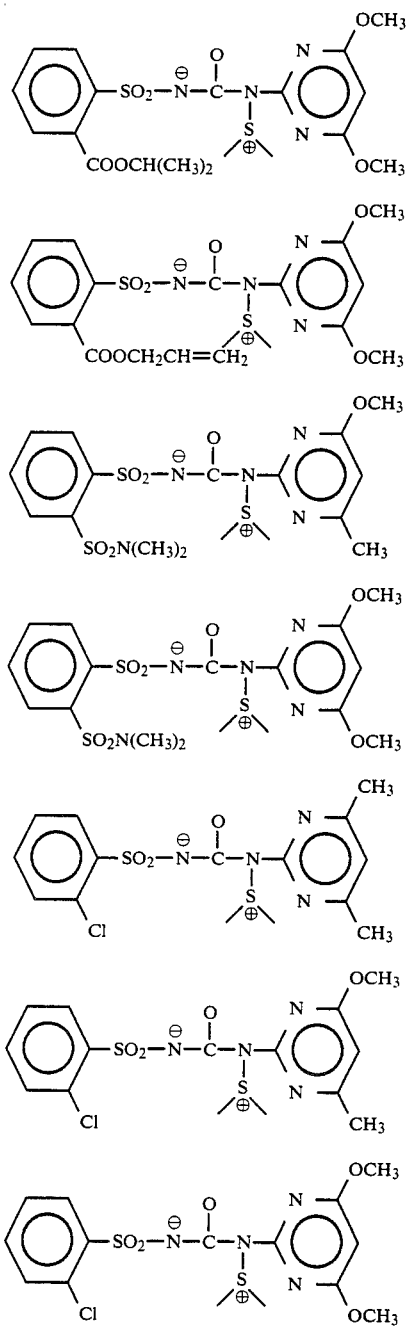

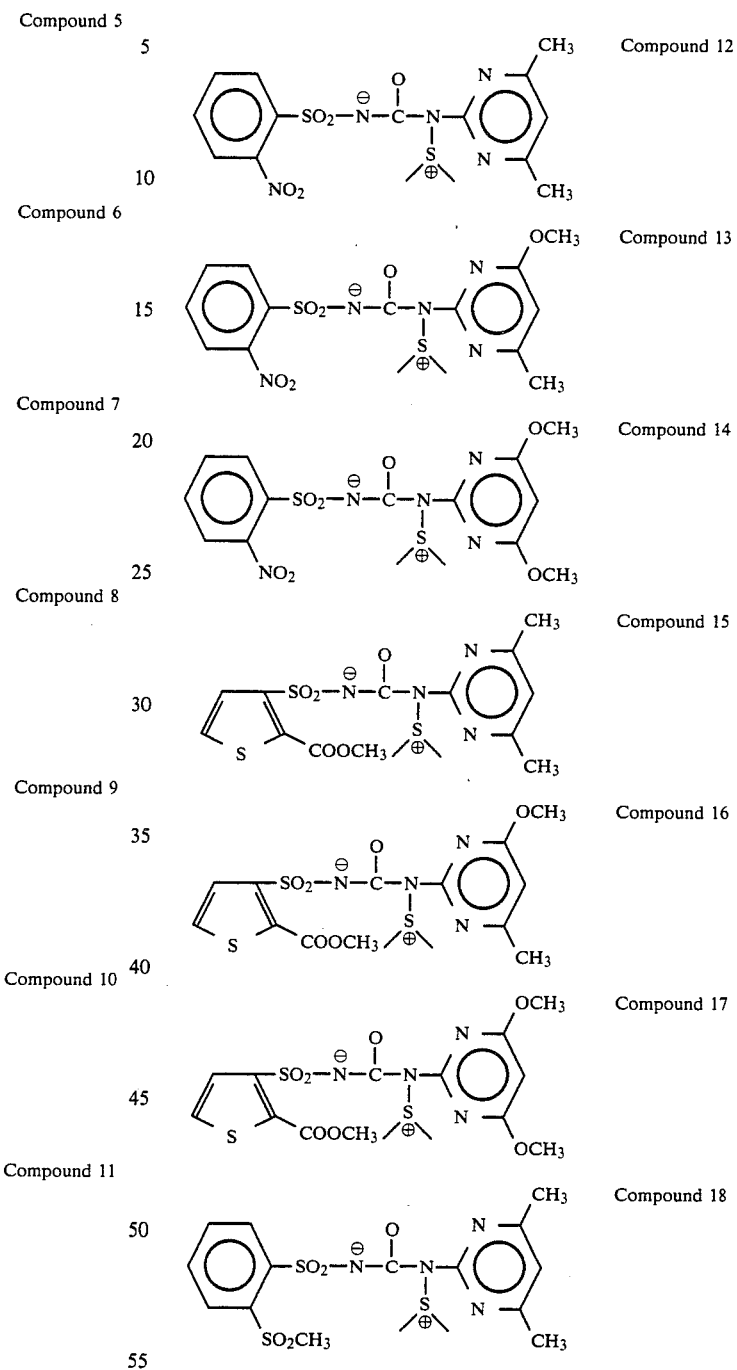

TABLE A

| Rate kg/ha | Cmpd. 1 0.4 | Cmpd. 2 0.4 | Cmpd. 3 0.4 | Cmpd. 4 0.4 | Cmpd. 5 0.4 | Cmpd. 6 0.4 | Cmpd. 7 0.4 | Cmpd. 8 0.4 | Cmpd. 9 0.4 | Cmpd. 10 0.4 |
|---|---|---|---|---|---|---|---|---|---|---|
| POST-EMERGENCE | | | | | | | | | | |
| Bush bean | 9C | 9C | 9C | 7C,9G,6Y | 6C,9G,6Y | 9D,9G,6Y | 9C | 8D,8G,6Y | 6C,9G,6Y | 9C |
| Cotton | 7C,9G | 9C | 5C,9G | 5C,9G | 4C,9G | 1C,5G | 9C | 6C,9G | 6C,9G | 9C |
| Morningglory | 10C | 10C | 9C | 10C | 1C,4G | 1C,5G | 9C | 3C,7G | 9C | 9C |
| Cocklebur | 10C | 9C | 2C,7G | 5C,9G | 3C,8H | 2C,9H | 10C | 3C,9H | 10C | 4C,9G |
| Sicklepod | 9C | 10C | 10C | 6C,9G | 3C,9G | 2C,6G | 9C | 6C,9G | 9C | 9C |
| Nutsedge | 9C | 9C | 10C | 1C,9G | 7C,9G | 3C,8G | 5C,9G | 10C | 10C | 3C,8G |
| Crabgrass | 9C | 9C | 4C,7G | 1C,7G | 2G | 3H | 6C,9G | 5C,9G | 7C,9G | 2C,8G |
| Barnyardgrass | 9C | 9C | 9C | 9C | 2C,7H | 3C,9H | 9C | 6C,9H | 9C | 9C |
| Wild Oats | 9C | 5C,9G | 1C,2G | 1C,9G | 0 | 0 | 9C | 1C | 3C,9G | 2C,9G |

TABLE A-continued

| | | | | | | | | | |
|---|---|---|---|---|---|---|---|---|---|
| Wheat | 6C,9G | 5U,9G | 1C,3G | 2C,9G | 0 | 0 | 5C,9G | 1C,9H | 1C,9G | 4C,9G |
| Corn | 10C | 9C | 7U,10C | 2C,9G | 2C,7H | 2H,9G | 5U,9C | 3U,9C | 3U,9C | 4U,9C |
| Soybean | 9C | 9C | 9C | 4C,9G | 3H | 2C,2H | 9C | 9C | 4C,9G | 5C,9G |
| Rice | 9C | 9C | 6C,9G | 5C,9G | 7G | 2C,9G | 6C,9G | 6C,9G | 6C,9G | 5C,9G |
| Sorghum | 10C | 10C | 9C | 3C,9G | 3C,9G | 2C,9H | 10C | 6C,9G | 9C | 4C,9G |
| Sugar beet | — | — | — | — | — | — | — | — | — | — |

| | Cmpd. 11 | Cmpd. 12 | Cmpd. 13 | Cmpd. 14 | Cmpd. 15 | Cmpd. 16 | Cmpd. 17 | Cmpd. 18 |
|---|---|---|---|---|---|---|---|---|
| Rate kg/ha | 0.4 | 0.4 | 0.4 | 0.4 | 0.4 | 0.4 | 0.4 | 0.4 |
| POST-EMERGENCE | | | | | | | | |
| Bush bean | 4C,8G,6Y | 3C,7G,6Y | 4C,8G,6Y | 2C,6G,6Y | 7C,9G,6Y | 7C,9G,6Y | 1C,1H | 9C |
| Cotton | 3C,3H,9G | 2C,8G | 3C,7G | 5C,9G | 6C,9G | 9C | 2C,3H,8G | 7C,9G |
| Morningglory | 5C,8G | 2C,7G | 2C,8G | 2C,8G | 2C,7G | 5C,9G | 1C,3G | 9C |
| Cocklebur | 4G | 7G | 5G | 2C | 5C,9G | 6C,9G | 4G | 6C,9G |
| Sicklepod | 3C,9G | 2C | 3G | 6C,9G | 1C | 1C,1H | 2C | 9C |
| Nutsedge | 5C,9G | 10C | 5G | 5C,9G | 9C | 2C,9G | 2C,4G | 10C |
| Crabgrass | 0 | 5C,8G | 3G | 0 | 2C,9H | 5C,9G | 0 | 9C |
| Barnyardgrass | 0 | 4C,6H | 7H | 0 | 5C,9H | 6C,9H | 2C,7H | 9C |
| Wild Oats | 0 | 0 | 2G | 0 | 1C | 5C,9H | 0 | 9C |
| Wheat | 0 | 0 | 3G | 0 | 2C,9G | 10C | 0 | 5C,9G |
| Corn | 2C,5G | 1U,8H | 2C,9H | 3C,8H | 1U,9H | 3C,9G | 2C,7H | 5U,9G |
| Soybean | 5C,9G | 1C,7H | 2H,6G | 3C,8H | 3G | 1H,3G | 4H | 5C,9G |
| Rice | 2G | 2C,9G | 9G | 0 | 3C,9G | 5C,9G | 6G | 6C,9G |
| Sorghum | 2G | 1C,6H | 2C,9H | 0 | 4C,9H | 2C,9G | 2C,9G | 10C |
| Sugar beet | — | — | — | — | — | — | — | — |

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 |
|---|---|---|---|---|---|---|---|---|---|---|
| Rate kg/ha | 0.4 | 0.4 | 0.4 | 0.4 | 0.4 | 0.4 | 0.4 | 0.4 | 0.4 | 0.4 |
| PRE-EMERGENCE | | | | | | | | | | |
| Morningglory | 2C,9G | 9C | 8G | 9G | 8G | 2C,5H | 9C | 7G | 9G | 9G |
| Cocklebur | 9H | 9H | 9H | 9H | — | 9H | 9H | 9H | 9H | 9H |
| Sicklepod | 2C,9G | 9G | 2C,8G | 9G | 2C,9G | 1C,4G | 9G | 1C,8G | 2C,9G | 9G |
| Nutsedge | 10E | 10E | 8G | 10E | 1C,5G | 2C,8G | 10E | 1C,7G | 10E | 5G |
| Crabgrass | 6C,9G | 3C,8G | 2C,5G | 1C,4G | 1C | 1C | 3C,9G | 3C,4G | 2C,7G | 1C,4G |
| Barnyardgrass | 6C,9H | 5C,9H | 6C,9H | 4C,9H | 3C,5H | 2C | 5C,9H | 6C,9H | 1C,9H | 9H |
| Wild Oats | 4C,9H | 5C,9H | 2C,8G | 2C,9G | 1C | 0 | 5C,9G | 3C,9G | 2C,9G | 9G |
| Wheat | 10E | 6C,9H | 2C,9G | 1C,9H | 0 | 0 | 5C,9H | 2C,9G | 2C,9G | 9G |
| Corn | 10E | 9H | 4C,8G | 2C,9G | 3C,7G | 2C,7G | 9H | 5C,8G | 10E | 4C,9G |
| Soybean | 9H | 9H | 1C,4H | 9H | 1C | 0 | 9H | 2C,6G | 3C,9H | 3C,8H |
| Rice | 10E | 10E | 10E | 9H | 3C,6G | 3C,8G | 10E | 10E | 10E | 10E |
| Sorghum | 10H | 5C,9H | 3C,8G | 5C,9H | 1C,3G | 1C | 8C,9H | 2C,9H | 7C,9H | 3C,9H |
| Sugar beet | — | — | — | — | — | — | — | — | — | — |

| | Cmpd. 11 | Cmpd. 12 | Cmpd. 13 | Cmpd. 14 | Cmpd. 15 | Cmpd. 16 | Cmpd. 17 | Cmpd. 18 |
|---|---|---|---|---|---|---|---|---|
| Rate kg/ha | 0.4 | 0.4 | 0.4 | 0.4 | 0.4 | 0.4 | 0.4 | 0.4 |
| PRE-EMERGENCE | | | | | | | | |
| Morningglory | 1C,7G | 1C,7G | 9G | 9G | 8G | 5C,9G | 2C,5G | 3C,9G |
| Cocklebur | 5C,9H | 2C,9H | 9H | 9H | 9H | 9H | 9H | 2C,9H |
| Sicklepod | 3C,9G | 2C,8G | 9G | 9G | 3G | 5G | 2C | 5C,9H |
| Nutsedge | 10E | 8G | 8G | 8G | 2C,8G | 9G | 2C,8G | 10E |
| Crabgrass | 3C | 1C,4G | 2G | 2C | 2C,7G | 2C,8G | 2C | 2C,9G |
| Barnyardgrass | 5C,6H | 6C,7H | 5C,9G | 2C,3H | 9H | 3C,9H | 5C,7H | 2C,9H |
| Wild Oats | 0 | 7G | 2C,7G | 0 | 2C,6G | 8G | 0 | 5C,9H |
| Wheat | 0 | 4G | 4G | 0 | 9H | 3C,9H | 2C | 5C,9H |
| Corn | 3C,5G | 2C,7G | 2C,8H | 2C,6G | 9H | 2C,9H | 2C,7G | 2C,9H |
| Soybean | 2C,3H | 2C,4H | 2C,6G | 2C | 2G | 1C,6H | 0 | 3C,9H |
| Rice | 5C,8H | 3C,9H | 8H | 4G | 10E | 10E | 10E | 10E |
| Sorghum | 0 | 2C,5G | 2C,5H | 1C | 3C,9H | 2C,9H | 6G | 6C,9H |
| Sugar beet | — | — | — | — | — | — | — | — |

Several of the compounds of this invention were further tested in a pre-emergence herbicide screen as described in Test B.

Test B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data for Compound 1 are summarized in Table B. Compound 1 appeared to be one of the most active of the compounds tested in this screen; however, the results for the other compounds tested indicate that they, too, have high herbicidal activity when applied at low rates as pre-emergence treatments on soil.

TABLE B

PRE-EMERGENCE ON WOODSTOWN SANDY LOAM

| | Compound 1 | | |
|---|---|---|---|
| Rate kg/ha | 0.03 | 0.12 | 0.008 |
| Crabgrass | 7G | 9G,5H | 2G |
| Barnyardgrass | 8G,9C | 9G,9C | 6G,3C |
| Sorghum | — | — | 9G |
| Wild Oats | 8G,8C | 10C | 7G |
| Johnsongrass | 9G,8C | 10C | 7G |
| Dallisgrass | 9G,3H | 9G,3H | 6G |
| Giant foxtail | 8G,5H | 9G,9C | 2G |
| Ky. bluegrass | 10E | 10E | 10C |
| Cheatgrass | 10C | 10C | 9G |
| Sugar beets | 7G,7C | 10C | 8G |
| Corn | 10C | 10C | 10C |
| Mustard | 9G,9C | 10C | 8G |
| Cocklebur | 7G,3H | 8G,5H | 6G |
| Pigweed | 10E | 10E | — |
| Nutsedge | 10E | 10E | 10C |
| Cotton | 9G,5H | 9G,5H | 6G |
| Morningglory | 7G | 9G,8C | 5G |
| Sicklepod | 6G | 8G,5C | 4G |
| Teaweed | 7G,3C | 8G,5C | 8G |
| Velvetleaf | 6G,3H | 9G,9C | 9G |
| Jimsonweed | 6G | 10C | 5G |
| Soybean | 7G,5H | 9G,8C | 6G |
| Rice | 10E | 10E | 10C |
| Wheat | 8G,8C | 10E | 3G |

A number of compounds were also tested to more accurately define their utility in post-emergence applications.

Test C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species, such as johnsongrass and field bindweed, are sometimes added to this standard test in order to evaluate unusual selectivity.

Again, Compound 1 appears to be one of the most active compounds when applied post-emergence, and the results for this compound are presented in Table C. All of the compounds tested, however, were shown to be highly active post-emergence herbicides. Some of the compounds, for example, Compounds 3, 4, 6 and 15, show potential utility for selective post-emergence weed control in wheat.

TABLE C

Over-the-Top Soil/Foliage Treatment

| | Compound 1 | | | |
|---|---|---|---|---|
| Rate kg/ha | 0.25 | 0.06 | 0.015 | 0.004 |
| Soybeans | 10C | 10C | 10C | 8G |
| Velvetleaf | 10C | 10C | 7G,8C | 2G |
| Sesbania | 10C | 10C | 10C | 9G |
| Sicklepod | 10C | 10C | 9G | 8G |
| Cotton | 10C | 10C | — | — |
| Morningglory | 10C | 10C | 1G | 1G |
| Alfalfa | 10C | 10C | 4G,4C | 5G,4C |
| Jimsonweed | 10C | 9G | — | 9G |
| Cocklebur | 10C | 9G | 8G | 7G |
| Sunflower | 10C | 9G,8C | 4G | 2G |
| Mustard | 9G,8C | — | 7G,1C | 4G |
| Sugar beets | 10C | 10C | 4C,7G | 5G,3C |
| Corn | 10C | 10C | 10C | 10C |
| Crabgrass | 8G | 9G | 10C | 5G,4C |
| Rice | 9G,6C | 9G,4C | 3G,2C | 4G |
| Nutsedge | 10C | 9G | 5G,4C | 3G |
| Barnyardgrass | 10C | 9G,8C | 8G | 7G |
| Wheat | 8G,6C | 7G | 7G,4C | 8G,7C |
| Giant Foxtail | 9G,6C | 9G,5C | — | 4G |
| Wild Oats | 7G,6C | 8G,6C | 4G | 4G |
| Sorghum | 8G,8C | 8G,8C | 8G,9C | 8G |
| Johnsongrass | 10C | 10C | 10C | 7C |
| Field Bindweed | 9G,4C | 9G,5C | 2C | 4G |

The procedure described as Test D was performed to illustrate the potential utility of Compound 3 as a post-emergence herbicide in wheat and barley.

Test D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descurainia pinnata*), smartweed (*Polygonum pensylvanicum*), tumble mustard (*Sisymbrium altissium*) kochia (*Kochia scoparia*), shepherd's purse (*Capsella bursa-pastoris*), Matricaria inodora, black nightshade (*Solanum nigrum*), yellow rocket (*Barbarea vulgaris*), rapeseed (*Brassica kaber*) and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The test compound applied was diluted with a non-phytotoxic solvent and sprayed over-the-top of the pans. An untreated control and a solvent alone control were included for comparison. The plantings were maintained in the greenhouse for 19–21 days at which time the treatment was compared to the controls and the effects visually rated. The recorded data are presented in Table D.

TABLE D

| | Compound 3 | |
|---|---|---|
| | Pre-Emergence | Post-Emergence |
| Rate kg/ha | | 0.12 |
| wheat | 0 | 0 |

TABLE D-continued

| | Compound 3 | |
|---|---|---|
| | Pre-Emergence | Post-Emergence |
| Rate kg/ha | | 0.12 |
| barley | 0 | 0 |
| wild oats | 0 | 0 |
| downy brome | 0 | 2G |
| cheatgrass | 2G | 2C,5G |
| blackgrass | 4G | 1C,4G |
| annual bluegrass | 4G | 4G |
| green foxtail | 0 | 5G |
| quackgrass | 2G | 7G |
| Italian ryegrass | 3G | 3G |
| ripgut brome | 3G | 3G |
| Russian thistle | 0 | 0 |
| tansy mustard | 9G | 2C,4G |
| *Galium aparine* | 2G | 0 |
| tumble mustard | 6G | 7C,9G |
| kochia | 0 | 3G |
| shepherd's purse | 8G | 3C,8G |
| *Matricaria inodora* | 7G | 3C,8G |
| black nightshade | 5G | 4G |
| yellow rocket | 5G | 2C,6G |
| wild mustard | 4G | 10C |
| wild buckwheat | 3G | 3G |

A final test was designed to evaluate the potential utility of compounds from within the scope of the invention for selective weed control in rice.

Test E

The crop was transplanted into simulated paddies containing soil and propagules of barnyardgrass (*Echinocholoa* sp.), water chestnut (*Eleocharis* sp.), and arrowhead (*Sagittaria* sp.). Three days after transplanting, the test chemicals were applied to the paddy water in a non-phytotoxic solvent at the rates shown in Table E. The paddies were maintained in a greenhouse, and plant response ratings were taken several weeks after application utilizing the rating system as described for Test A. Compounds 11 and 14 appear to have utility for weed control in transplanted rice.

TABLE E

| | Compound 11 | Compound 14 | |
|---|---|---|---|
| Rate, grams/hectare | 100 | 25 | 100 |
| Rice | 1G | 0 | 0 |
| Barnyardgrass | 9C | 7C | 8C |
| Water Chestnut | 10C | 0 | 0 |
| Arrowhead | 6G,5H | 0 | 0 |

What is claimed is:

1. A compound of the formula:

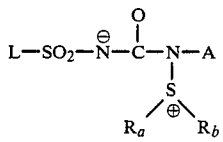

wherein
$R_a$ is $CH_3$ or $CH_2CH_3$;
$R_b$ is $CH_3$ or $CH_2CH_3$;
L is

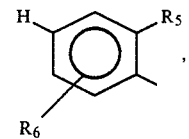

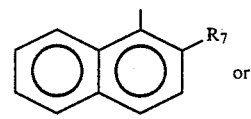

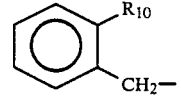

$R_5$ is $C_1$-$C_4$ alkyl, $C_1$-$C_4$ alkoxy, $OCH_2CH_2OCH_3$, F, Cl, Br, $NO_2$, $CF_3$, $CO_2R_{19}$, $SO_2NR_{20}R_{21}$, $SO_2N(OCH_3)CH_3$, $OSO_2R_{22}$, $S(O)_nR_{23}$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OCH_2CH_3$, $C_6H_5$,

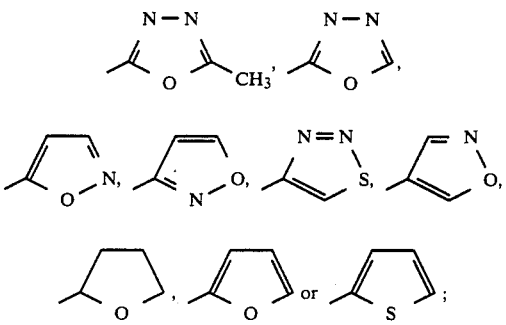

$R_6$ is H, F, Cl, Br, $CF_3$, $CH_3$, $OCH_3$, $SCH_3$ or $OCF_2H$;
$R_7$ is H, $CH_3$, $OCH_3$, F, Cl, Br, $OSO_2CH_3$ or $S(O)_nCH_3$;
$R_{10}$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;
$R_{19}$ is $C_1$-$C_4$ alkyl, $CH_2CH_2OCH_3$, $CH_2CH_2Cl$ or $CH_2CH=CH_2$;
$R_{20}$ is $C_1$-$C_3$ alkyl;
$R_{21}$ is $C_1$-$C_3$ alkyl;
$R_{22}$ is $C_1$-$C_3$ alkyl or $N(CH_3)_2$;
$R_{23}$ is $C_1$-$C_3$ alkyl or $CH_2CH=CH_2$;
n is 0 or 2; and
W is O, S or $SO_2$;
A is

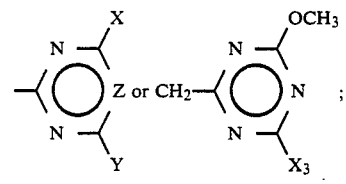

X is $CH_3$, $OCH_3$, $OCH_2CH_3$, $OCF_2H$, $CH_2F$ or $CF_3$;

Y is H, $CH_3$, $OCH_3$, $OCH_2CH_3$, $CH_2OCH_3$, $CH_2OCH_2CH_3$, $N(CH_3)_2$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $SCF_2H$, $CR_{24}(QCH_3)_2$,

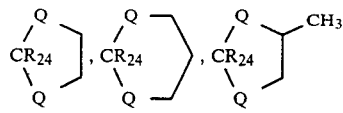

or $CR_{24}(QCH_2CH_3)_2$; Q is O or S;

$R_{24}$ is H or $CH_3$;

Z is N;

$X_3$ is $CH_3$ or $OCH_3$; provided that the total number of carbon atoms of $R_{20}$ and $R_{21}$ is less than or equal to four.

2. A compound of claim 1 where A is A-1.

3. A compound of claim 2 where Y is $CH_3$, $OCH_3$, $OCH_2CH_3$, $CH_2OCH_3$, $OCH_2CF_3$ or $CH(OCH_3)_2$ and X is $CH_3$, $OCH_3$, or $CF_3$.

4. A compound of claim 3 where L is L-1, or L-2.

5. A compound of claim 4 where L is L-1; $R_5$ is $OCH_3$, $OCH_2CH_3$, Cl, $NO_2$, $CF_3$, $CO_2CH_3$, $CO_2CH_2CH_3$, $SO_2N(CH_3)_2$, $SO_2N(OCH_3)CH_3$, $OSO_2R_{22}$, $S(O)_nR_{23}$, $OCF_2H$, $SCF_2H$, $OCH_2CH=CH_2$, $OCH_2C\equiv CH$,

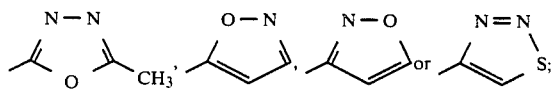

$R_{22}$ is $C_1-C_3$ alkyl; $R_{23}$ is $CH_3$ and n is 2.

6. Compounds of claim 4 where L is L-2 and $R_7$ is Cl, $CH_3$, $OCH_3$, $SCH_3$ or Br.

7. A composition suitable for controlling the growth of undesired vegetation comprising an effective amount of a compound of claim 1 and at least one of the following: surfactant, solid or liquid inert diluent.

8. A composition suitable for controlling the growth of undesired vegetation comprising an effective amount of the compound of claim 3 and at least one of the following: surfactant, solid or liquid inert diluent.

9. A composition suitable for controlling the growth of undesired vegetation comprising an effective amount of the compound of claim 4 and at least one of the following: surfactant, solid or liquid inert diluent.

10. A composition suitable for controlling the growth of undesired vegetation comprising an effective amount of the compound of claim 5 and at least one of the following: surfactant, solid or liquid inert diluent.

11. A method of controlling the growth of undesired vegetation comprising applying to the locus of said vegetation an effective amount of a compound of claim 1.

12. A method of controlling the growth of undesired vegetation comprising applying to the locus of said vegetation an effective amount of the compound of claim 3.

13. A method of controlling the growth of undesired vegetation comprising applying to the locus of said vegetation an effective amount of the compound of claim 4.

14. A method of controlling the growth of undesired vegetation comprising applying to the locus of said vegetation an effective amount of the compound of claim 5.

* * * * *